US008110604B2

(12) United States Patent
Awad

(10) Patent No.: US 8,110,604 B2

(45) **Date of Patent: *Feb. 7, 2012**

(54) METHODS AND COMPOSITION FOR TREATING A MATERIAL

(75) Inventor: Aziz C. Awad, Westland, MI (US)

(73) Assignee: UrthTech, LLC, Farmington Hills, MI (US)

( * ) Notice: Subject to any disclaimer, the term of this patent is extended or adjusted under 35 U.S.C. 154(b) by 1607 days.

This patent is subject to a terminal disclaimer.

(21) Appl. No.: 11/486,736

(22) Filed: Jul. 14, 2006

(65) Prior Publication Data

US 2011/0081300 A1 Apr. 7, 2011

(51) Int. Cl.

| | |
|---|---|
| ***A61K 31/20*** | (2006.01) |
| ***A61K 31/045*** | (2006.01) |
| ***A61K 33/00*** | (2006.01) |
| ***A61L 2/00*** | (2006.01) |

(52) U.S. Cl. ........ 514/558; 514/560; 514/724; 424/722; 422/28

(58) Field of Classification Search .................. 514/558, 514/560, 724; 424/722; 422/28

See application file for complete search history.

(56) References Cited

U.S. PATENT DOCUMENTS

| | | | |
|---|---|---|---|
| 3,282,776 | A | 11/1966 | Kitzke et al. |
| 3,835,057 | A | 9/1974 | Cheng et al. |
| 4,200,655 | A | 4/1980 | Farah et al. |
| 4,446,153 | A | 5/1984 | Yang |
| 4,678,658 | A | 7/1987 | Casey et al. |
| 4,695,453 | A | 9/1987 | Tuominen et al. |
| 4,714,563 | A | 12/1987 | Kajs et al. |
| 4,883,659 | A | 11/1989 | Goodman et al. |
| 4,956,175 | A | 9/1990 | Maignan et al. |
| 5,180,749 | A | 1/1993 | Cusack et al. |
| 5,827,511 | A | 10/1998 | Campbell et al. |
| 5,879,470 | A | 3/1999 | Murch et al. |
| 6,013,270 | A | 1/2000 | Hargraves et al. |
| 6,022,551 | A | 2/2000 | Jampani et al. |
| 6,080,387 | A | 6/2000 | Zhou et al. |
| 6,106,854 | A | 8/2000 | Belfer et al. |
| 6,248,343 | B1 | 6/2001 | Jampani et al. |
| 6,376,448 | B1 | 4/2002 | Colurciello, Jr. et al. |
| 6,566,574 | B1 | 5/2003 | Tadros et al. |
| 6,617,294 | B2 | 9/2003 | Narula et al. |
| 6,638,492 | B1 | 10/2003 | Matacotta et al. |
| 6,821,940 | B2 | 11/2004 | Bullock et al. |
| 7,754,766 | B2 * | 7/2010 | Awad ........................... 514/560 |
| 2004/0022867 | A1 | 2/2004 | Tucker et al. |
| 2004/0213750 | A1 | 10/2004 | Bennett et al. |
| 2005/0202137 | A1 | 9/2005 | Awad |
| 2005/0271595 | A1 | 12/2005 | Brown |
| 2009/0324514 | A1 * | 12/2009 | Awad ............................. 424/49 |

FOREIGN PATENT DOCUMENTS

| | | | |
|---|---|---|---|
| DE | 3027644 | A1 | 4/1982 |
| EP | 82110376.9 | | 11/1982 |
| EP | 83303799.7 | | 6/1983 |
| EP | 0414309 | | 8/1990 |
| EP | 0689767 | | 1/1996 |
| EP | 0848907 | | 6/1998 |
| EP | 2070552 | A1 | 6/2009 |
| WO | WO 00/05330 | | 2/2000 |
| WO | WO 2009/074330 | A1 | 6/2009 |

OTHER PUBLICATIONS

Extended European Search Report, dated Jul. 30, 2010, for Application No. 07809766.4-2103/2040540, PCT/US2007014486.

Humfeld, H., "Antibiotic Activity of the Fatty-Acid-Like Constituents of Wheat Bran", Journal of Bacteriology, V. 54, No. 4, Oct. 1, 1947, pp. 513-517.

Rutala and Weber, Disinfection and Sterilization in Healthcare Facilities, 2004.

Boyce and Pittet, Guideline for Hand Hygiene in Health-Care Settings,Recommendationsof the Healthcare Infection Control Practices Advisory Committee and the HICPAC/SHEA/APIC/ IDSAHand Hygiene Task Force, 2002.

Page et al., Morbidity& Mortality Weekly Report, Public Health Dispatch: Update: Cutaneous Anthra in a Laboratory Worker—Texas,2002.

Rosenberg et al., Health Care Issues, Precautions in Handling Tissues, Fluids, and Other Contaminated Materials from Patients with Documented or Suspected Creutzfeldt-JakobDisease, 1986.

Brown, Kathryn, Up in the Air, Science, vol. 305, pp. 1228-1229, 2004.

Weiss, Peter, Ghost Town Busters, Science News, vol. 168, pp. 282-284, 2005.

Hsu, Spencer, Cost of Anthrax Cleanup on Hill, The Washington Post, A Section; p. A07, Mar. 7, 2002.

Castelleni et al., American Academy of Neurology, Early Pathologic and Biochemical Changes in Creutzfeldt-JakobDisease: Study of Brain Biopsies, 1996.

Beekes, Michael, et al., "Fast, broad-range disinfection of bacteria, fungi, viruses and prions" Journal of General Virology (2010), 91, 580-589.

Written Opinion of the International Searching Authority for PCT/ US2007/014486 completed on Aug. 20, 2008.

* cited by examiner

*Primary Examiner* — Raymond Henley, III

(74) *Attorney, Agent, or Firm* — Ian C. McLeod

(57) ABSTRACT

A composition and method are described for sanitizing or otherwise treating a material such as a non-living surface, living tissue, soil or atmosphere which may be contaminated by a toxin, chemical warfare agent, insect, prion, microorganism or other infectious agent. Also described are methods of making the composition.

42 Claims, 19 Drawing Sheets

EFFECT OF 100% FB ON THE REDUCTION OF BLACK MOLD SPORES

CONTROL 100% FB (1 min contact time)

EFFECT OF 60% FB ON THE REDUCTION OF BLACK MOLD SPORES

CONTROL 60% FB (1 min contact time)

EFFECT OF 50% FB ON THE REDUCTION OF BLACK MOLD SPORES

CONTROL 50% FB (1 min contact time)

EFFECT OF 40% FB ON THE REDUCTION OF BLACK MOLD SPORES

CONTROL 40% FB (1 min contact time)

EFFECT OF 30% FB ON THE REDUCTION OF BLACK MOLD SPORES

CONTROL 30% FB (1 min contact time)

EFFECT OF 12.5% NaOCl ON THE KILLING OF BLACK MOLD SPORES

CONTROL

NaOCl (1 min contact time)

EFFECT OF 7.5% NaOCl ON THE KILLING OF BLACK MOLD SPORES

CONTROL NaOCl (1 min contact time)

EFFECT OF 3.75% NaOCl ON THE KILLING OF BLACK MOLD SPORES

CONTROL NaOCl (1 min contact time)

Inoculated with *Stachybotrys*

Inoculated/Treated with composition (50% FB)

Inoculated with *Stachybotrys*

Inoculated/Treated with Household Clorox bleach

Inoculated with *Stachybotrys*

Inoculated/Treated with composition (50% FB)

Inoculated with *Stachybotrys*

Inoculated/Treated with Household Clorox® bleach

Inoculated with *Stachybotrys*

Inoculated/Treated with composition (50% FB)

Inoculated with *Stachybotrys*

Inoculated/Treated with Household Clorox® bleach

Not treated

Inoculated with *Stachybotrys*

Not treated

Inoculated with *Stachybotrys*

Not treated

Inoculated with *Stachybotrys*

CONTROL (Not treated)

Inoculated with Black Mold Spores

Inoculated with Black Mold Spores

Inoculated/Treated with 50% FB

Inoculated with Black Mold Spores

Inoculated/Treated with NaOCl

METHODS AND COMPOSITION FOR TREATING A MATERIAL

CROSS-REFERENCE TO RELATED APPLICATION

This application is related to U.S. application Ser. No. 12/380,077, filed Feb. 23, 2009, now U.S. Pat. No. 7,754,766 and pending U.S. application Ser. No. 12/387,120, filed Apr. 28, 2009, which is a continuation-in-part of application Ser. No. 12/380,077 (now U.S. Pat. No. 7,754,766) and application Ser. No. 11/486,736.

STATEMENT REGARDING FEDERALLY SPONSORED RESEARCH OR DEVELOPMENT

Not Applicable

Reference to a "Computer Listing Appendix Submitted on a Compact Disc"

Not Applicable.

BACKGROUND OF THE INVENTION (1) Field of the Invention

This invention relates to compositions and methods for sanitizing or otherwise treating a material. The compositions improve the decontaminating effect of lower alkanols containing 1 to 6 carbon atoms ($C_1$-$C_6$). The compositions disinfect or otherwise sanitize materials such as living tissues (skin, hands, etc.) and inanimate objects (instruments, medical equipment, military and civilian facilities, furniture, papers and printed materials, etc.) of harmful contaminants including, but not limited to chemical warfare agents (VX, mustard, sarin, soman, and tabun), toxins, protozoa, insects (e.g., disease vectors), and pathogenic infectious agents such as bacteria, fungi, viruses, fungal and bacterial spores, and conformationally altered prions (CJD, CWD, BSE, Scrapie).

(2) Description Of Prior Art

Germicides include both antiseptics and disinfectants. Antiseptics are germicides applied to living tissue and skin while disinfectants are antimicrobials applied only to inanimate objects. In general, antiseptics are only used on the skin and not for surface disinfection, and disinfectants are not used for skin antisepsis because they may cause injury to skin and other tissues (Rutala and Weber, 2004).

In the past, disinfecting hard surfaces did not require a major decision: You could use a standard powder detergent, bleach or an abrasive powder. End of discussion. Nowadays, hard-surface disinfectants fill entire store aisles and include many specialized products such as bathroom, toilet bowl, glass, ceramic, and kitchen disinfectants of varying kinds, powder and cream scourers, and wipes. One reason for the increase in the number of hard-surface disinfectants is the simple fact that today's hard surfaces include many more types of materials than in the past. For example, in the past, kitchens and bathrooms were primarily finished in wood and other natural surfaces, the modern counterparts contain stainless steel, plastic, fiberglass, ceramics, marble, enamel and porcelain, to name just a few, creating new disinfecting challenges.

On the other hand, recently, there has been renewed emphasis placed on hand hygiene and skin wellness as a result of the Centers for Disease Control and Prevention (CDC)'s "Guideline for Hand Hygiene in Healthcare Settings." Hand hygiene is the single most important action that can help reduce the spread of infection in hospitals. The CDC's National Nosocomial Infections Surveillance system (NNIS), which collects data from some three hundred hospitals, estimates that in U.S. hospitals there are two million healthcare-associated infections each year accounting for nearly 90,000 deaths annually and $4.5 billion in excess healthcare costs. Current literature documents unacceptably low levels of hand hygiene among healthcare workers (HCWs). There are a number of reasons that impact HCWs compliance to hand washing: (1) lack of easy accessibility to sinks; (2) hand washing causes dry, irritated hands; (3) HCWs are too busy to wash their hands with soap and water often enough; (4) lack of knowledge on when hand hygiene should take place, including casual contact, before and after gloving, etc.

Soaps are detergent-based products that contain esterified fatty acids and sodium or potassium hydroxide. Plain soaps have minimal, if any, antimicrobial activity. In several studies, hand washing with plain soap failed to remove pathogens from the hands of hospital personnel and, occasionally, plain soaps have become contaminated, which may lead to colonization of hands of personnel with gram-negative bacilli (Boyce and Pittet, 2002). Alcohol hand sanitizers have been introduced into healthcare facilities to help HCWs adhere to the recommended hand hygiene guidelines. The CDC legitimated alcohol-based sanitizers because it recognized that the efficacy of alcohol sanitizers was greater than soap and water in reducing the number of germs on hands. However, alcohols are not recommended for sterilizing medical and surgical materials principally because of their lack of sporicidal action and their inability to penetrate protein-rich materials (Rutala and Weber, 2004). The majority of alcohol-based hand antiseptics contain either isopropanol, ethanol, n-propanol, or a combination of two of these products. The majority of studies of alcohols have evaluated individual alcohols in varying concentrations. Other studies have focused on combinations of two alcohols or alcohol solutions containing limited amounts of hexachlorophene, quaternary ammonium compounds, povidone-iodine, triclosan, or chlorhexidine gluconate.

U.S. Pat. No. 4,200,655 to Farah, et al. discloses compositions containing benzyl alcohol as active ingredient intended for topical virucidal use both in vivo and in vitro, especially for use on the hands and especially for preventing transmission of rhinoviruses.

U.S. Pat. No. 4,446,153 to Yang discloses a skin sanitizing composition particularly suited as teat dip or udder wash for dairy cows comprising at least one phenyl alkanol as the antiseptic ingredient.

U.S. Pat. No. 4,695,453 Tuominen, et al. discloses thickened alcoholic antibacterial compositions containing preferably ethanol, propanol, and benzyl alcohol as active ingredients.

U.S. Pat. No. 4,956,175 Maignan, et al. discloses the use of high alcohol content antimicrobial gel compositions for disinfecting hands possessing moisturizing and conditioning agents.

U.S. Pat. No. 6,022,551 to Jampani, et al. discloses an antimicrobial composition comprising an antimicrobial selected from the group consisting of more than 30% by volume alcohol and an effective amount of triclosan; and an effective amount of phenoxy ethanol, an effective amount of benzalkonium chloride or benzethonium chloride; and an effective amount of PHOSPOLIPID CDM. This antimicrobial composition is intended for topical use, such as the hands.

U.S. Pat. No. 6,248,343 to Jampani, et al. relates to antimicrobial compositions which additionally provide therapeutic benefits to the skin. It discloses an antimicrobial composition comprising an antimicrobial selected from the group consisting of more than 30% by volume alcohol, an effective amount of triclosan and mixtures thereof; an effective amount of phenoxy ethanol, an effective amount of benzalkonium chloride or benzethonium chloride; and an effective amount of PHOSPOLIPID CDM; and an effective amount of a naturally occurring plant or extract thereof.

U.S. Pat. No. 6,617,294 to Narula et al. describes a waterless sanitizing hand cleanser comprising an effective amount of alcohol to produce a reduction in microorganisms on the surface of the skin, and emollients or oils for skin moisturizing.

U.S. Pat. Appl. Publication No. 2005/0271595 to Brown discloses a sanitizing composition in the form of a viscous liquid or gel suitable for use as a hand wash composition comprising alcohol, water, a thickener, and antimicrobial agents.

Eur. Pat. Appl. No. 82110376.9 describes an aqueous sterilizing agent for foods or food processing machines and utensils, comprising ethanol and at least one alkaline substance as active ingredients.

Eur. Pat. Appl. No. 83303799.7 relates to aqueous disinfectant solutions with residual biocidal activity for disinfecting hard surfaces in hospitals, comprising from 60 to 80% v/v of $C_1$ to $C_4$ alkanol and at least two antimicrobial agents with a combined concentration in the solution of up to 2% w/v. The first antimicrobial agent is a biguanide compound and the second is a quaternary ammonium compound.

U.S. Pat. No. 4,678,658 to Casey, et al. describes an aerosol spray for use in disinfecting a surface with a fine spray consisting essentially of lower alkyl alcohol, a disinfecting surfactant, a pH sensitive dye, and alkali means for adjusting the pH of the fluid to produce a color in the liquid so upon the fast neutralization by air the dye loses color.

U.S. Pat. No. 5,180,749 to Cusack, et al. discloses an aqueous antimicrobial composition that includes up to about 30 percent by weight ethyl alcohol and about 2 to 5 percent by weight of benzyl alcohol and the remainder to 100% water, and a method of use of the composition for destroying or reducing the number of microbes on an inanimate surface contaminated therewith.

U.S. Pat. Appl. Publication No. 2004/0213750 to Bennett et al. discloses an aqueous hard surface antimicrobial treatment compositions comprising an alcohol and an a pH adjusting agent such the pH range of the composition is from about 7.0 to about 13.0.

U.S. Pat. Appl. Publication No. 2005/0202137 to Awad describes a method for sanitizing red meat for human consumption with an aqueous solution containing lower alkanol and pH modifying agents.

U.S. Pat. No. 6,821,940 to Bullock, et al. describes premoistened wipes containing a substrate and a cleaning composition using toxicologically-acceptable ingredients for treating food such as produce, e.g., fruits and vegetables, edible animal proteins, toys, baby highchairs and the like.

The widespread prevalence of health-care associated diarrhea caused by *Clostridium difficile* and the recent occurrence in the United States of human *Bacillus anthracis* infections (11 cases inhalation anthrax and 11 cases of cutaneous anthrax) as a result of the intentional exposure to *Bacillus anthracis* via contaminated letters has raised concerns regarding the activity of antiseptic and disinfectant agents against spore-forming bacteria. More recently, a laboratory worker acquired anthrax as a result of contact with the surface of vials containing *Bacillus anthracis* (Page et al., 2002). None of the agents reported in the prior art (including alcohols, chlorhexidine, hexachlorophene, iodophors, PCMX, and triclosan) whether used in antiseptic (hand-wash or hand-rub) preparations or in hard surface disinfectants are reliably sporicidal against *Clostridium* spp. or *Bacillus* spp. (Boyce and Pittet, 2002). Moreover, some of these agents (e.g., triclosan) have been linked to antibiotic-resistant bacteria in lab tests. Examples of sporicidal reagents, using relatively high concentrations, include glutaraldehyde, formaldehyde, chlorine oxyacids compounds, peroxy acids, and ethylene oxide. In general, all of these compounds are considered to be toxic. On the other hand, all the chemical antimicrobial agents reported in the prior art (whether sporicidal or not), including ethylene oxide sterilization, ethanol, formalin, beta-propiolactone, detergents, quaternary ammonium compounds, Lysol® disinfecting solution (Reckitt Benckiser, Berkshire, UK), alcoholic iodine, acetone, potassium permanganate, hydrogen peroxide and chlorine dioxide, are ineffective in inactivating the infectivity of conformationally altered infectious prions (Rosenberg et al., 1986) and, their effect on chemical warfare agents is not reported.

Terrorists' threats involving chemical and biological agents, in the context of weapon of mass destruction, are of great concerns to national defense and local law enforcement. For decades, these worries were the quiet domain of U.S. military and national weapon labs, funded by the Department of Energy or the Defense Advanced Research Projects Agency. Future bioterror weapons, scientists say, could include genetically engineered pathogens, prions, and bioregulators (Brown, 2004). During a simulated dirty-bomb attack staged in Seattle in the spring of 2003, one of the lessons learned that responders had nothing to stop the spread of radioactive dust (Weiss, 2005). By the same token, the spread of biological and chemical warfare agents, should a terrorist attack occur, is also very hard, if not impossible, to contain using the technology of the prior art. Should a large scale attack take place, its perpetrators will probably be monitoring the speed and efficacy of the clean-up to decide the value of launching another attack. The anthrax decontamination of the Hart Senate Office Building (Hsu, 2002), using chlorine dioxide, has raised concerns about the readiness to deal with large scale biological attacks. Chlorine dioxide and sodium hypochlorite (household bleach) are used for disinfection of environmental surfaces and are not used as antiseptics applied to skin.

U.S. Pat. No. 6,566,574 to Tadros, et al. teaches the use of an aqueous formulation for neutralizing both chemical and biological agents. The formulation comprises at least two solubilizing agents (a cationic surfactant such as quaternary ammonium salts and a cationic hydrotrope such as tetrapentyl ammonium bromide), at least one reactive compound and water to produce an aqueous formulation. The technical problems associated with this technology include: (1) the need for a different formulation for each specific chemical and biological agent; (2) it has no effect on infectious prions; (3) it cannot be used on living tissues, e.g., topical treatment on skin due to the corrosiveness and toxicity of the reagents used; (4) it cannot be used to decontaminate food products, in case of an agroterrorist attack, because the reagents used are not food grade (GRAS); and (5) it cannot be used in health-care facilities as a hand sanitizer to replace soap and water.

U.S. Pat. Appl. Publication No. 2004/0022867 to Tucker et al. teaches the use of an aqueous formulation for neutralizing toxants which comprises at least two solubilizing agents (a cationic surfactant and a cationic hydrotrope), a reactive compound (selected from the group consisting of hydrogen peroxide, urea hydrogen peroxide, hydroperoxycarboante, peracetic acid, sodium perborate, sodium peroxypyrophosphate, sodium peroxysilicate, and percarbonate), a bleaching activator, and a sorbent additive. The technical issues associated with this technology include: (1) preparation of the composition in the field due to the instability of the bleaching activator; (2) short shelf life (about eight hours), therefore, it cannot be used in healthcare facilities as a hand sanitizer to replace soap and water; (3) have no effect on infectious prions; (4) it cannot be used on wounds, e.g., topical treatment on wounded skin due to the corrosiveness and toxicity of the reagents used; and (5) it cannot be used to decontaminate food products, in case of an agroterrorist attack, because the reagents used are not food grade (GRAS).

Collectively, the prior art has recognized the real and continuing need for a single, effective, general, safe for humans and the environment, and easy to use formulation for decontaminating both inanimate objects and living tissues of harmful contaminants consisting of chemical warfare (VX, mustard, sarin, soman, and tabun), toxins, insects (e.g., disease vectors), and pathogenic infectious agents such as bacteria, fungi, viruses, fungal and bacterial spores, and conformationally altered prions (CJD, CWD, BSE, Scrapie).

OBJECTS

It is an object of the present invention to provide compositions and methods for sanitizing a material. These and other objects will become increasingly apparent by reference to the following discussion.

SUMMARY OF THE INVENTION

The present invention provides a method for improving the germicidal and sporicidal spectra and activities of lower alkanols ($C_1$-$C_6$) for disinfecting living tissues (skin, hands, etc.) and inanimate objects (instruments, papers and printed materials, medical equipment, hard surfaces, military and civilian facilities, etc.) with unprecedented speed, economy, safety, gentleness, and residual antimicrobial effects. Further, the present invention provides a lower alkanol ($C_1$-$C_6$) composition that can decontaminate skin/wound following chemical and biological warfare (CBW) agent exposure to contain, and destroy the CBW preventing cutaneous penetration and further contamination. The composition can decontaminate fresh produce such as apples, baby carrots, strawberry, hard cheese blocks, shell eggs, and fresh red meat carcasses to eliminate infectious agents such as conformationally altered prions, bacteria, fungi, parasites and viruses to provide the highest possible health protection standards to the consumers. Further still, the composition can be used to decontaminate animal by-products used in feeds, and therefore replace traditional rendering techniques. Further still, the composition can be used to decontaminate homes, building materials, and furniture infected with black mold spores. The composition can be used for insect vector control (e.g. mites, mosquitoes etc.) to reduce the transmission of infectious pathogens. Further still, the composition contains materials that are affirmed as GRAS (Generally Recognized As Safe), e.g., food-grade, to protect against possible misuse by the consumer.

Thus, the present invention provides a method for sanitizing a material which comprises: (a) providing an aqueous composition which comprises a mixture of a lower alkanol containing 1 to 6 carbon atoms and a fatty acid derivative which is a salt or ester at a pH of about 14 or above, wherein the fatty acid derivative is between about 0.1% and 25% by weight of the composition; and (b) applying the composition to the material in an effective amount to sanitize the material; and optionally removing a resulting composition of step (b).

In further embodiments of the method the fatty acid derivative is an alkali or alkaline earth metal salt. In further embodiments, the fatty acid is a sodium (Na), potassium (K), lithium (Li), calcium (Ca) or magnesium (Mg) salt. In still further embodiments, the fatty acid derivative is an alkali or alkaline metal salt of a fatty acid comprising 4 to 22 carbon atoms. In still further embodiments, the fatty acid derivative is an alkali or alkaline metal salt of lauric acid. In still further embodiments, the fatty acid derivative is potassium laurate. In still further embodiments, the fatty acid derivative is an ester selected from the group consisting of a butyl ester, ethyl ester, methyl ester, fatty acyl-Coenzyme A, sucrose ester and a monoglyceride. In still further embodiments, the monoglyceride comprises a glycerol moiety attached by ester or ether linkage to one or more fatty acids having from 4 to 22 carbon atoms or to one or more saturated or unsaturated fatty alcohols having from 8 to 16 carbon atoms. In still further embodiments, the toxin is a *Stachybotrys* toxin. In further embodiments, the microorganism or other infectious agent is a fungus, a bacteria, a fungal spore, a bacterial spore, a virus or a conformationally altered prion. In still further embodiments, the fungal spore is a *Stachybotrys chartarum* spore. In still further embodiments, the bacterial spore is a *Bacillus atropheus* spore. In still further embodiments, the chemical warfare agent is VX, mustard, sarin, soman, or tabun. In still further embodiments, the conformationally altered prion selected from the group consisting of CJD, CWD, BSE, and Scrapie.

The present invention provides a composition which comprises in a mixture: a lower alkanol containing 1 to 6 carbon atoms; and a fatty acid derivative which is a salt or ester soluble in the alkanol, wherein the composition has a pH of 14 or above wherein the fatty acid derivative is between about 0.1% to 25% by weight of the composition. In further embodiments, the composition is provided as an aqueous solution. In further embodiments, the lower alkanol is methanol, ethanol, n-propanol, isopropanol, n-butanol or mixtures thereof. In further embodiments, the fatty acid derivative is an alkali or alkaline earth metal salt. In still further embodiments, the fatty acid is a sodium (Na), potassium (K), lithium (Li), calcium (Ca) or magnesium (Mg) salt. In still further embodiments, the fatty acid derivative is an alkali or alkaline metal salt of a fatty acid comprising 4 to 22 carbon atoms. In still further embodiments, the fatty acid derivative is an alkali or alkaline metal salt of lauric acid. In still further embodiments, the fatty acid derivative is potassium laurate. In still further embodiments, the fatty acid derivative is an ester selected from the group consisting of a butyl ester, ethyl ester, methyl ester, fatty acyl-Coenzyme A, sucrose ester and a monoglyceride. In still further embodiments, the monoglyceride comprises a glycerol moiety attached by ester or ether linkage to one or more fatty acids having from 4 to 22 carbon atoms or to one or more saturated or unsaturated fatty alcohols having from 8 to 16 carbon atoms. In still further embodiments, the composition further comprises one or more ingredients selected from the group consisting of thickeners, emollients, moisturizers, corrosion inhibitors, propellants, perfumes, flavoring agents, defoamers, antioxidants and dyes.

The present invention provides a method of treating a material, which comprises: (a) providing an aqueous composition which comprises a mixture of a lower alkanol containing 1 to 6 carbon atoms and a fatty acid derivative which is a salt or ester at a pH of about 14 or above, wherein the fatty acid derivative is between about 0.1% and 25% by weight of the composition; and (b) applying the composition to the material in an effective amount to treat the material. In further embodiments, a resulting composition of step (b) is removed from the material.

The present invention provides a method of making a composition, which comprises: providing a lower alkanol containing 1 to 6 carbon atoms; providing a fatty acid derivative which is a salt or ester soluble in the alkanol; and mixing the lower alkanol and fatty acid derivative to provide the composition, wherein the composition has a pH of 14 or above and wherein the fatty acid derivative is between about 0.1% to 25% by weight of the composition. In still further embodiments, the lower alkanol is ethanol. In still further embodiments, the fatty acid derivative is an alkali or alkaline earth metal salt. In still further embodiments, the fatty acid is a sodium (Na), potassium (K), lithium (Li), calcium (Ca) or magnesium (Mg) salt. In still further embodiments, the fatty acid derivative is an alkali or alkaline metal salt of a fatty acid comprising 4 to 22 carbon atoms. In still further embodiments, the fatty acid derivative is an alkali or alkaline metal salt of lauric acid. In still further embodiments, the fatty acid derivative is potassium laurate. In still further embodiments, the fatty acid derivative is an ester selected from the group consisting of a butyl ester, ethyl ester, methyl ester, fatty acyl-Coenzyme A, sucrose ester and a monoglyceride. In still further embodiments, the monoglyceride comprises a glycerol moiety attached by ester or ether linkage to one or more fatty acids having from 4 to 22 carbon atoms or to one or more saturated or unsaturated fatty alcohols having from 8 to 16 carbon atoms.

The present invention provides a method of making a composition, which comprises: providing a lower alkanol containing 1 to 6 carbon atoms; providing a fatty acid; providing an alkalinating agent; and mixing the lower alkanol, fatty acid and alkalinating agent to provide the composition, wherein the composition has a pH of 14 or above and wherein the fatty acid derivative is between about 0.1% to 25% by weight of the composition. The lower alkanol is ethanol. In still further embodiments, the fatty acid is a fatty acid comprising 4 to 22 carbon atoms. In still further embodiments, the fatty acid is lauric acid. In still further embodiments, the alkalinating agent is selected from the group consisting of an alkali metal hydroxide, alkaline earth metal hydroxides, alkali metal or hydrogen carbonates and mixtures thereof. In still further embodiments, the alkalinating agent is selected from the group consisting of ammonium hydroxide, aluminum hydroxide, sodium hydroxide, potassium hydroxide, lithium hydroxide, calcium hydroxide, magnesium hydroxide, sodium carbonate, sodium hydrogen carbonate, and mixtures thereof.

BRIEF DESCRIPTION OF THE DRAWINGS

FIG. 1A shows the effect of 100% FB on the reduction of black mold spores. FIG. 1B shows the effect of 60% FB on the reduction of black mold spores. FIG. 1C shows the effect of 50% FB on the reduction of black mold spores. FIG. 1D shows the effect of 40% FB on the reduction of black mold spores. FIG. 1E shows the effect of 30% FB on the reduction of black mold spores.

FIG. 3A shows the effect of 12.5% NaOCl on the killing of black mold spores. FIG. 3B shows the effect of 7.5% NaOCl on the killing of black mold spores. FIG. 3C shows the effect of 3.75% NaOCl on the killing of black mold spores.

FIGS. 11A and 11B show the inoculation of black mold spores on wood as the porous material. FIGS. 11C and 11D show the performance of 50% FB sprayed onto wood. FIGS. 11E and 11F show the effect of 1.84% sodium hypochlorite sprayed onto wood.

DETAILED DESCRIPTION OF THE INVENTION

Figure 1A:
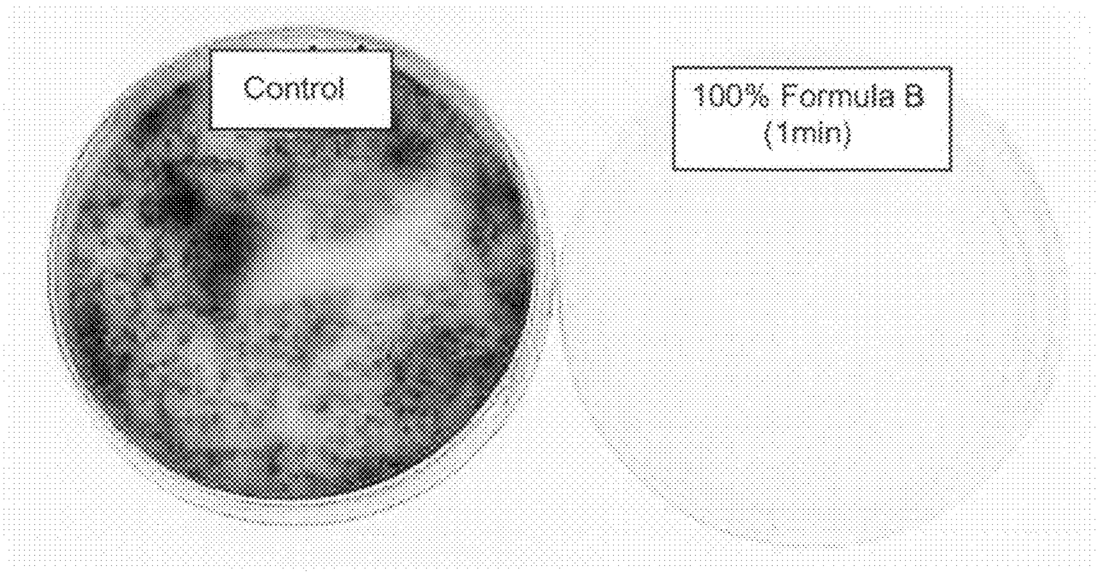
FIGS. 1A-E show the effect of different concentrations of composition FB on the killing of black mold (*Stachybotrys chartarum*) spores.

All patents, patent applications, government publications, government regulations, and literature references cited in this specification are hereby incorporated herein by reference in their entirety. In case of conflict, the present description, including definitions, will control.

The term "CFU" as used herein refers to colony forming units.

The term "treat" as used herein is a broad term meaning to coat, change, alter, vary, and/or modify a material so that the material becomes different in one or more aspects from the starting material. The term can refer to a physical and/or chemical change including, but not limited to, those resulting from a chemical reaction, solubilization and/or emulsification are also encompassed by the term.

The term "FB" as used herein refers to one embodiment of the composition of the present invention as set forth in Table 1.

The term "material" as used herein refers to any solid, liquid and/or gaseous matter, such as but not limited to air, a chemical, a non-living surface, living tissue, soil or an atmosphere.

The term "sanitizing" as used herein refers to decreasing or eliminating the level or detrimental capacity of agents that are capable of being injurious to health of a living animal. Some examples of agents capable of being injurious to health of a living animal are contaminants, such as but not limited to toxins, chemical warfare agents, insects, prions, microorganisms or other infectious agents. Examples of sanitizing include chemical modification and degradation, however removal of the agents by solubilizing is also encompassed by the term.

The present invention provides compositions and methods to improve the decontaminating effect of lower alkanols containing 1 to 6 carbon atoms ($C_1$-$C_6$) for sanitizing materials such as, but not limited to living tissues (skin, hands, etc.) and inanimate objects (instruments, medical equipment, military and civilian facilities, furniture, papers and printed materials, etc.) of harmful contaminants such as but not limited to chemical warfare agents (VX, mustard, sarin, soman, and tabun), toxins, protozoa, insects (e.g., disease vectors), and pathogenic infectious agents such as bacteria, fungi, viruses, fungal and bacterial spores, and conformationally altered prions (CJD, CWD, BSE, Scrapie). The continuing challenge in developing new germicides is to strike a balance between safety, convenience, and efficacy. The ease of use and safety are as important, and sometimes more important, than using the best efficacious chemical technologies. Bacterial spores, fungal spores, and infectious prions are highly resistant to chemical and physical disinfecting agents. Processes designed to achieve sterilization of food, pharmaceutical, medical, and other products have thus, of necessity, had to take this high level of resistance into account. From this scheme, it can be envisaged that activity against the more resistant infectious agents (e.g., *Bacillus atropheus* spores and infectious prions) implies activity against the least resistant infectious agents (e.g., vegetative bacteria, lipid viruses).

U.S. Patent Application Publication No. 2005/0202137 (application Ser. No. 11/031,935) to Awad, hereby incorporated herein by reference in its entirety, teaches a method for treating biological tissue, particularly meats for human consumption, so as to sanitize the tissue. The method inactivates microorganisms and pathogenic prions (proteins) in the tissue. The method of sanitizing comprises treating the tissue with an aqueous solution selected from the group consisting of an alkali metal hydroxide, alkaline earth metal hydroxide and mixtures thereof and a lower alkanol containing 1 to 6 carbon atoms such that any prions in contact with the solution are inactivated. The present invention describes a method for improving the decontaminating properties of lower alkanols $C_1$-$C_6$ by mixing them with GRAS constituents essentially comprising fatty acids derivatives, alkalinating agents, water and mixtures thereof. Optionally, one or more ingredient selected from the group consisting of thickeners, emollients, moisturizers, corrosion inhibitors, defoamers, flavoring agents, propellants, perfumes, antioxidants, and dyes can be added. The resulting compositions can be used for disinfecting living tissues (skin, hands, etc.) and inanimate objects (instruments, medical equipment, military and civilian facilities, furniture, papers and printed materials, etc.) of harmful contaminants consisting of chemical warfare agents (VX, mustard, sarin, soman, and tabun), toxins, protozoa, insects (ie., disease vectors), and pathogenic infectious agents such as bacteria, fungi, viruses, fungal and bacterial spores, and conformationally altered prions (CJD, CWD, BSE, Scrapie).

Moreover, the activity of the compositions is retained for a considerable time after the evaporation of the solvent. In a biological weapon attack, the first step has to be to prevent further migration of the pathogens. Immobilizing biological warfare agents (e.g., bacterial spores, etc.) may also enable rescue workers to do their jobs without becoming contaminated. A very important aspect of the present invention is that the film that results after the evaporation of the solvent will physically entrap bacterial or fungal spores, and therefore prevent the resuspension of spores, which is a major cause of transmission of infection and contamination of environmental surfaces. The compositions of this invention can be very easily prepared by simply mixing measured amounts of the necessary constituents with the lower alkanols followed by any optional ingredients and packaging.

The lower alkanols ($C_1$-$C_6$) useful in the present invention are selected from the group consisting of, but not limited to, methanol, ethanol, n-propanol, isopropanol, n-butanol, and mixtures thereof which are present in an amount of from about 3 and 95%. Ethanol or isopropanol is most preferred. Examples of suitable fatty acid derivatives that would be useful for the present invention include alkali and alkaline earth metal salt (Na, K, Li, Mg etc.) of fatty acids containing 4 to 22 carbon atoms. Other fatty acids derivatives useful herein include ester derivatives such as butyl-, ethyl-, methyl esters, fatty acyl-Coenzyme A, sucrose esters, and monoglycerides of a desirable fatty acid.

The monoglycerides useful for the present invention are glycerol moieties attached by ester or ether linkage to fatty acids having from 4 to 22 carbon atoms ($C_4$-$C_{22}$) or to either saturated or unsaturated fatty alcohols having from 8 to 16 carbon atoms ($C_8$-$C_{16}$). Generally, the inclusion of fatty acid derivatives in amounts from 0.1% by weight to about 25% by weight, especially from 5 to 10% by weight have been observed to be useful. Lauric acid derivatives are most preferred.

In some preferred embodiments, the alkalinating agents are selected from the group comprising ammonium hydroxide, aluminum hydroxide, alkali metal hydroxides (Na, K, Li), alkaline earth metal hydroxides (Ca, Mg), alkali metal or hydrogen carbonates, e.g., sodium carbonate or sodium hydrogen carbonate, or mixtures thereof. Generally, the quantity of the alkalinating agents may vary from 0.01% by weight to 10% by weight, and most preferably within the range of 3 to 6% by weight, e.g. 5% by weight.

The compositions of the present invention include water as solvent and most preferably deionized water. The quantity of water may vary from about 5 to 95% by weight, and most preferably within the range of 15 to 60% by weight. The compositions can optionally include thickeners selected from the group consisting of, but are not limited to, fumed silica, xanthan gum, pectin, guar gum, hydroxylpropyl cellulose, gelatin, natural gums, polyethylene glycol, polypropylene glycol, carboxypolymethylene, Acrylates/C10-30 alkyl acrylate crosspolymer, and water soluble waxes; such ingredient may be included in any effective amount. The compositions can also optionally include one or more corrosion inhibitors. Examples of suitable corrosion inhibitors include mono- and triethanolamine, dicyclohexyl amine nitrite, and N,N-dibenzylamine, and such ingredient may be included in any effective amount.

The compositions of the present invention can optionally be formulated with emollients and/or moisturizers. Emollients and/or moisturizers which may be used are well known and conventional in the art and include, but are not limited to, propylene glycol, isopropyl myristate, glycerin, acetamidopropyl trimonium chloride. Such ingredient may be included in any effective amount. The compositions can also optionally be formulated with conventional propellants for dispensing as aerosols for conventional pressurized containers. Examples of suitable propellants include, but are not limited to, isobutene, n-butane, propane, dimethyl ether and mixtures thereof; such ingredient may be included in any effective amount. In addition, the compositions can optionally include one or more perfumes. Any material that provides a desirable scent may be used. Especially preferred are oils derived from citrus fruit, e.g., orange, lemons, limes, etc. which contain large amounts of terpenes. Such ingredient can be included in any effective amount.

The compositions of the present invention can optionally include one or more defoamers. Examples of suitable defoamers include, silicone (e.g., polydimethyl siloxane), $C_8$ to $C_{18}$ aliphatic alcohol or $C_9$ to $C_{12}$-alkyl substituted phenol or a mixture thereof. The compositions can also optionally include one or more antioxidants. Examples of suitable antioxidants include, but are not limited to, tocopherols (e.g., vitamin E, or tocopherol acetate), vitamin C and mixtures thereof. The ingredients can be included in any effective amount. The compositions can also optionally include one or more dyes. Examples of suitable dyes include, but are not limited to, pH dependent dyes (e.g., blue dye thymophtalein), nonstaining dye, and such ingredient can be included in any effective amount. The compositions can also optionally include one or more flavoring agents. Any material that provides a desirable flavor can be used, and the ingredient can be included in any effective amount.

The present invention incorporates the combined effect of certain GRAS constituents on the decontaminating activity of lower alkanols $C_1$-$C_6$ for the purpose of improving the germicidal and sporicidal spectra and activities of these alkanols. Constituents tested in the examples herein were selected from the standpoint of safety and include fatty acids derivatives, alkalinating agents, water and mixtures thereof. Optionally, one or more ingredients selected from thickeners, emollients, moisturizers, corrosion inhibitors, propellants, perfumes, flavoring agents, defoamers, antioxidants, and dyes are also included in the composition. The compositions of the present invention attack pathogens at multiple points in their life cycles with more than one antimicrobial compound. The antimicrobial compounds inactivate pathogens, acting not only individually but also acting additionally and synergistically. The compositions disclosed herein are non-corrosive, non-toxic, and can be incorporated into a wide variety of carriers. Therefore, they can be packaged in aerosol form in conventional aerosol containers, fog generating devices, or in liquid form in trigger pumps spray bottles and squeeze bottles (liquid/gel). They can be impregnated into towelettes (woven or non-woven nature) and packaged individually or packaged in bulk for individual dispensing to satisfy a wide variety of operational objectives.

The present invention provides an aqueous formulation to improve the decontaminating properties of lower alkanols $C_1$-$C_6$ for disinfecting living tissues and inanimate objects of harmful contaminants. The composition of the present invention includes lower $C_1$-$C_6$ alkanols including, but not limited to, methanol, ethanol, n-propanol, isopropanol, n-butanol, and mixtures thereof which are present in an amount of from about 3 and 95%. Ethanol or isopropanol is most preferred. The composition also includes fatty acid derivatives including, but not limited to, alkali and alkaline earth metal salts (Na, K, Li, Mg etc.) of fatty acids having 4 to 22 carbon atoms, and mixtures thereof. Other useful fatty acids derivatives include ester derivatives such as butyl-, ethyl-, methyl esters, fatty acyl-Coenzyme A, sucrose esters, and monoglycerides of a desirable fatty acid. The monoglycerides useful for the present invention are glycerol moieties attached by ester or ether linkage to fatty acids having from 4 to 22 carbon atoms ($C_4$-$C_{22}$) or to either saturated or unsaturated fatty alcohols having from to 16 carbon atoms ($C_8$-$C_{16}$), and mixtures thereof. Generally, the inclusion of fatty acid derivatives in amounts from 0.1% by weight to about 25% by weight, especially from 5 to 10% by weight have been observed to be useful. Lauric acid derivatives are most preferred. Alkalinating agents include, but are not limited to, ammonium hydroxide, aluminum hydroxide, alkali metal hydroxides (Na, K, Li), alkaline earth metal hydroxides (Ca, Mg), alkali metal or hydrogen carbonates, e.g., sodium carbonate or sodium hydrogen carbonate, or mixtures thereof. Generally, the quantity of the alkalinating agents may vary from 0.01% by weight to 10% by weight, and most preferably within the range of 3 to 6% by weight, e.g. 5% by weight. And optionally, one or more constituents selected from the group consisting of thickeners, emollients, moisturizers, corrosion inhibitors, propellants, perfumes, flavoring agents, defoamers, antioxidants, and dyes.

The harmful contaminants acted upon by the present invention include chemical warfare agents (VX, mustard, sarin, soman, and tabun), toxins, insects (e.g., disease vectors), and pathogenic infectious agents such as bacteria, fungi, viruses, fungal and bacterial spores, and conformationally altered prions (CJD, CWD, BSE, Scrapie). The inanimate objects acted upon include, but are not limited to, instruments, medical equipment, military and civilian facilities, furniture, papers and printed materials, etc. stainless steel, plastic, fiberglass, ceramics, marble, enamel and porcelain.

In some embodiments, the solvent is water. In further embodiments, the alkanol is ethanol. In some embodiments, the solvent is ethanol. In further embodiments, the contaminant is a chemical warfare agent, biological warfare agent, protein, (e.g., infectious prions), a toxin, (e.g., *Stachybotrys* toxins, botulinum), an insect, (e.g., disease vectors), a pathogenic infectious agent (such as bacteria, fungi, viruses), a fungal spore, (e.g., *Stachybotrys chartarum*) or a bacterial spore (e.g., *Bacillus atropheus* spore). In further embodiments, the contaminant is on a surface, in the atmosphere, in soil, on medical and surgical instruments, on food products, in animal feeds, in papers and printed materials, on military equipment or in living tissues including, but not limited to, skin, hands, muscle, biological tissues from animal and plant origin.

The following examples are intended to promote a further understanding of the present invention. The compositions of the invention are illustrated by examples of specific formulations as described below without, however, being limited thereto. It is to be understood that these examples are provided by way of illustration only and that further useful formulations falling within the scope of the present invention may be readily produced by one skilled in the art without deviating from the scope of the invention.

Example 1

TABLE 1

| Component | Composition (FB) | Amount |
|---|---|---|
| Alkanol (ml): | Ethanol | 62 |
| Fatty acid (g): | Lauric acid | 10 |
| Alkalinating agent (g): | Potassium hydroxide | 3.5 |
| Water (ml): | Deionized | 26 |
| pH: | | 14.42 |

The mixture was made up to a volume of 100 ml with deionized water.

The following summary of results and data is based on tests performed on black mold spores using the composition (FB) of Table 1. *Stachybotrys chartarum*, commonly known as the “black house-mold”, has become a major problem in homes and office buildings, costing the building and insurance industries billions of dollars each year. The fungus grows best on cellulose containing materials such as mill paper, fiber board, wood and gypsum board, in moist warm environments such as homes previously subjected to water damage from condensation, leakage and flooding. There are nearly 120 million housing units and million commercial buildings in the U.S. that are potentially susceptible to this water damage. Individuals who have come in contact with *Stachybotrys* contaminated straw or grains and found to be infected, manifests symptoms such as dermatitis, pain and inflammation of the mucous membranes of the mouth and throat, a burning sensation of the nasal passages, tightness of the chest, cough, bloody rhinitis, fever, headache, rash, and fatigue. Those who consumed contaminated grains reported a burning sensation in the mouth, nausea, vomiting, diarrhea and abdominal pain. *Stachybotrys* has been implicated in both the "sick building syndrome", and pulmonary hemorrhage in infants. This fungus produces a number of trichothecene mycotoxins, amongst which are the satratoxins (G, F and H), roridin, trichodermol and trichoverrol. Although the mode of action of satratoxin is not well understood, it is thought to be an immunosuppressant even at very low concentrations, as well as a potent protein synthesis inhibitor. Remediation typically involves demolition and removal of *Stachybotrys* contaminated areas. Destruction of this fungus and its toxins with the composition of the present invention will greatly reduce remediation costs.

Fungal Spore Preparation: *Stachybotrys chartarum* spores which were determined to be highly toxic and satratoxin extracts with known satratoxin concentration (ng/g), were used in this experiment. A known concentration of *Stachybotrys* spores was sub-cultured on potato dextrose agar (PDA) or malt extract agar (MEA) plates. The plates were incubated in the dark at room temperature (26° C.) for five to seven (5-7) days, until confluent growth was achieved. Spores were collected with phosphate buffer saline (PBS), pH 7.0, with final concentrations of $10^5$ and $10^7$ spores/ml of phosphate buffered saline (PBS).

Determination of Treatment Efficacy: Spores. Nine milliliters (ml) of the composition (FB) was inoculated with one milliliter (1 ml) of spore concentration. Initial spore concentration was 6.65 log colony forming units per ten milliliters (CFU/10 ml) solution. Sampling was done in sterile test tubes. Tubes were agitated vigorously, three times per minute for the first ten minutes and then once every five minutes for a total of ten (10), thirty (30), and sixty (60) minutes. The tubes were then emptied and rinsed three times with deionized water (5 ml) for five minutes (5 min) each, in the same manner, as the treatment was performed. Solutions from each treatment were combined. Positive (spores inoculated without experimental treatments) and negative (experimental treatments without spores) controls were included. One hundred microliters (μl) from the combined solution of each treatment was plated on PDA plates at room temperature in the dark for seven days. This procedure was replicated three times. Spores were counted after a week.

Figure 1B:
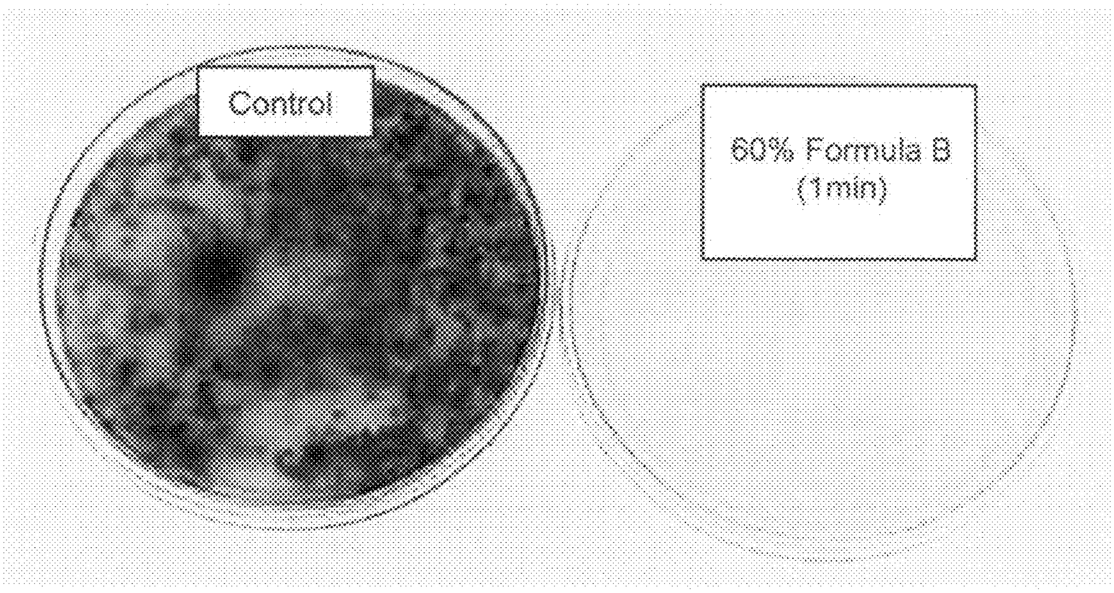
Figure 1C:
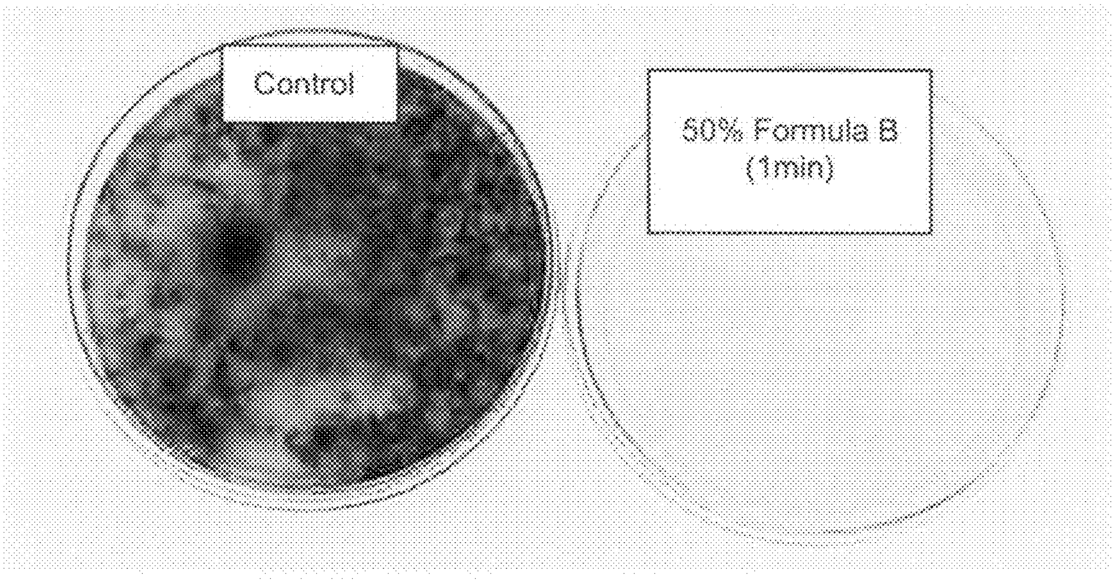
Figure 1D:
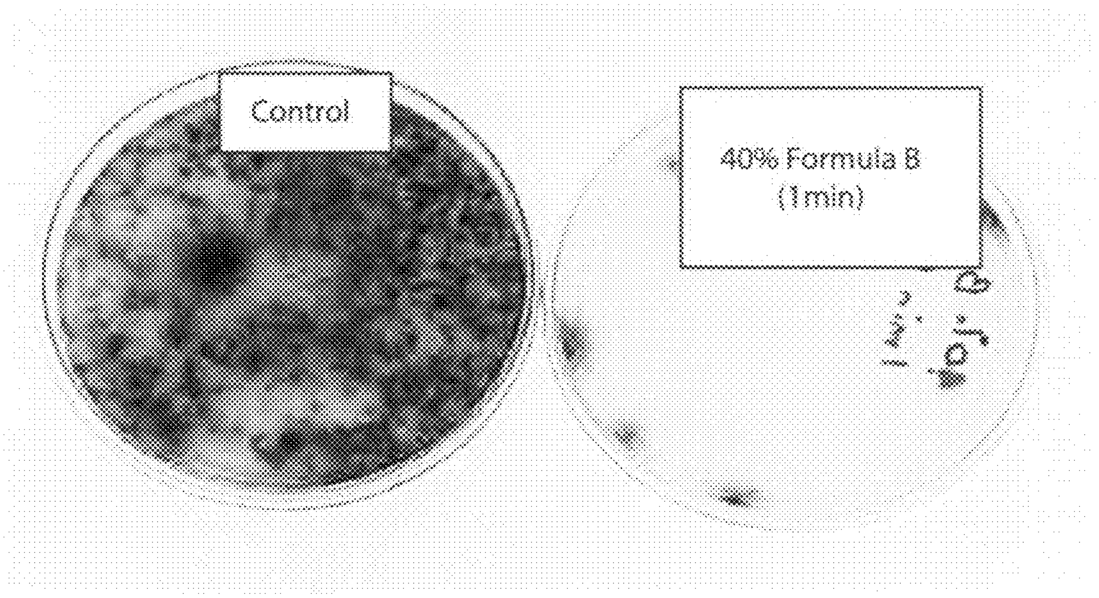
Figure 1E:
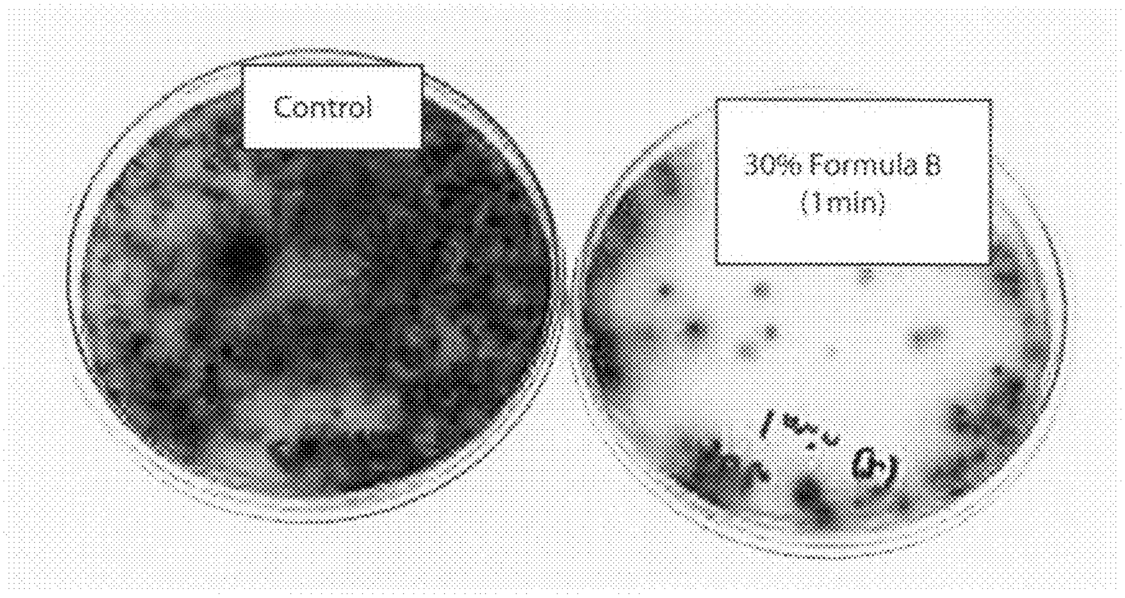
Figure 2:
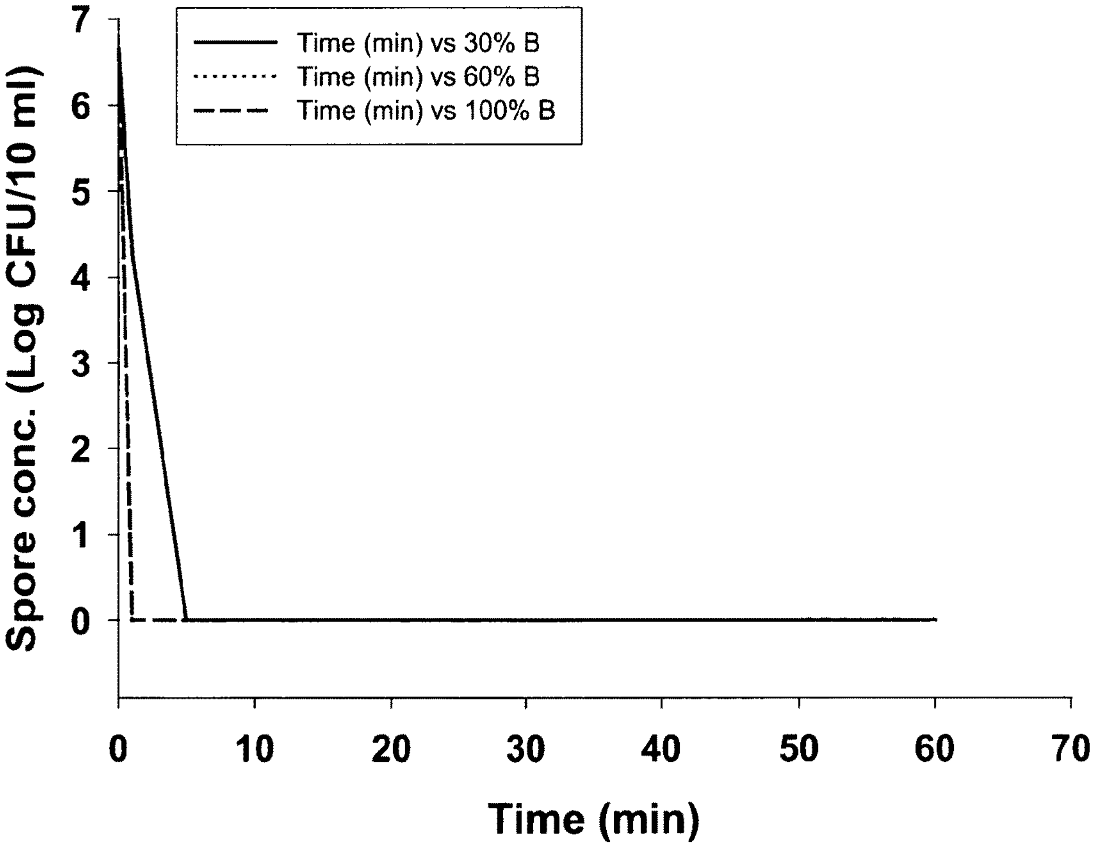
FIG. 2 is a graph showing the effect of different concentrations (30, 60, and 100%) of composition (FB) on the killing of black mold (*Stachybotrys chartarum*) spores.
Figure 10:
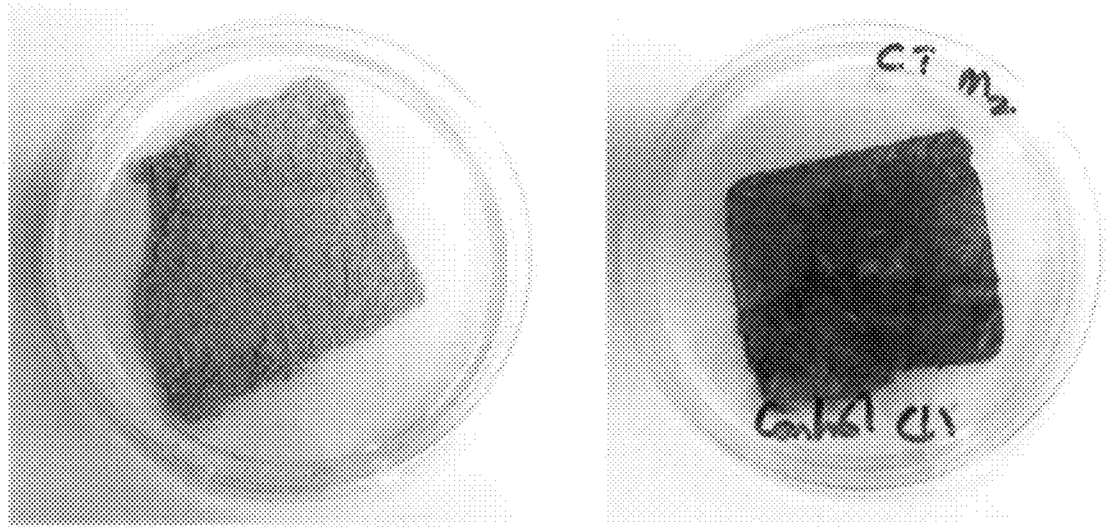
FIG. 10 shows the growth of black mold on ceiling tiles inoculated with *Stachybotrys chartarum* spores and incubated for 30 days in the dark.
Figure 11A:
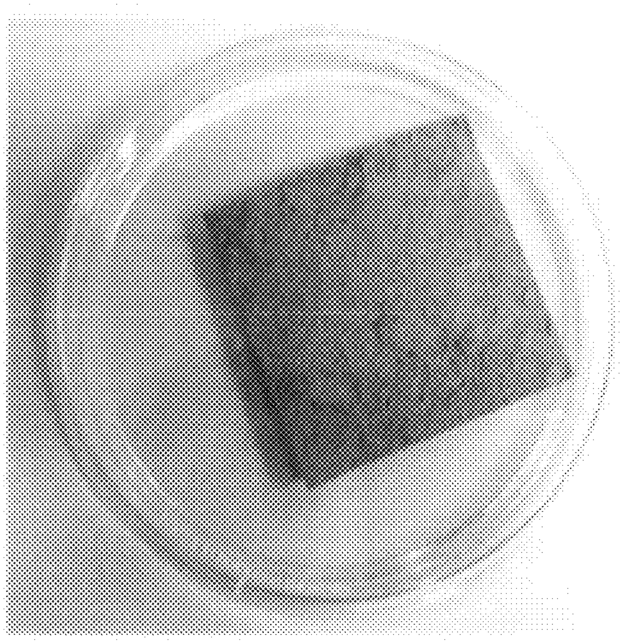
FIGS. 11A-F show the effect of spraying composition FB on wood after inoculation of the wood with black mold (*Stachybotrys chartarum*) spores.
Figure 11B:
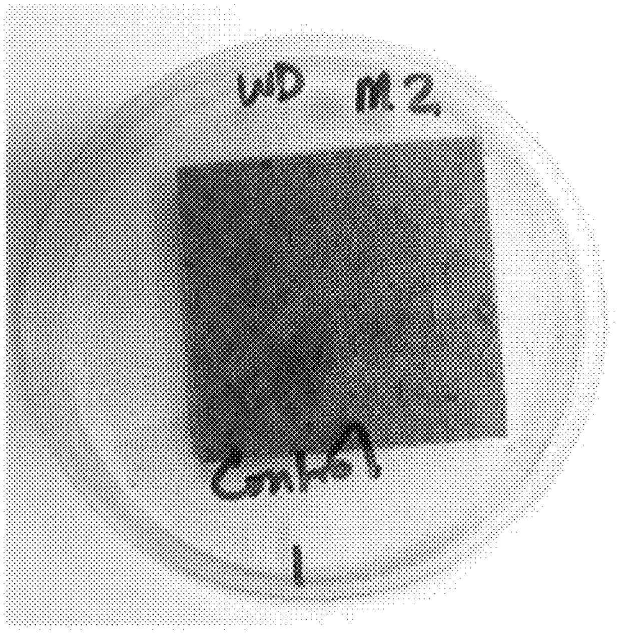
Figure 11C:
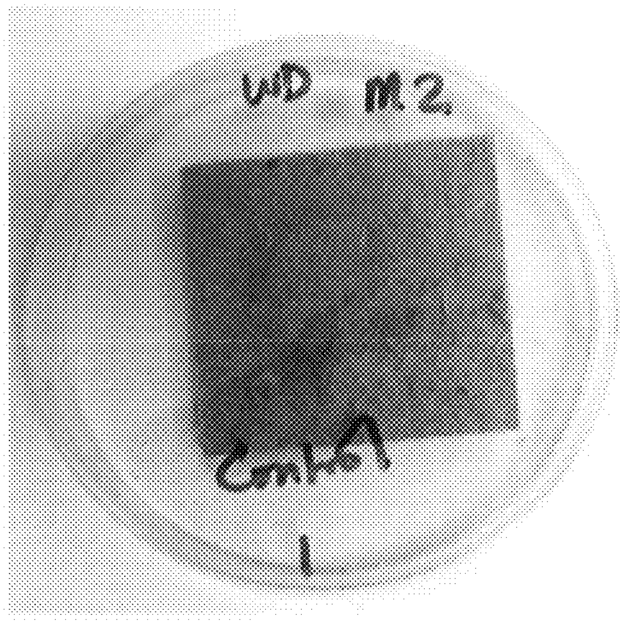
Figure 11D:
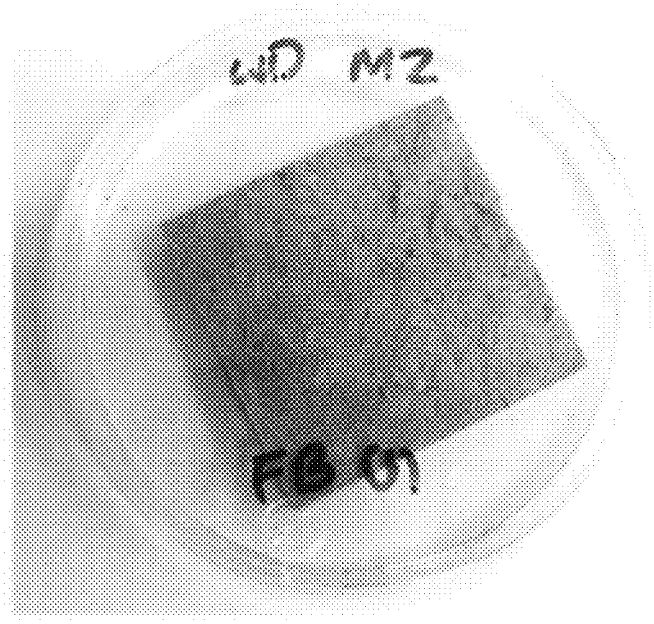
Figure 11E:
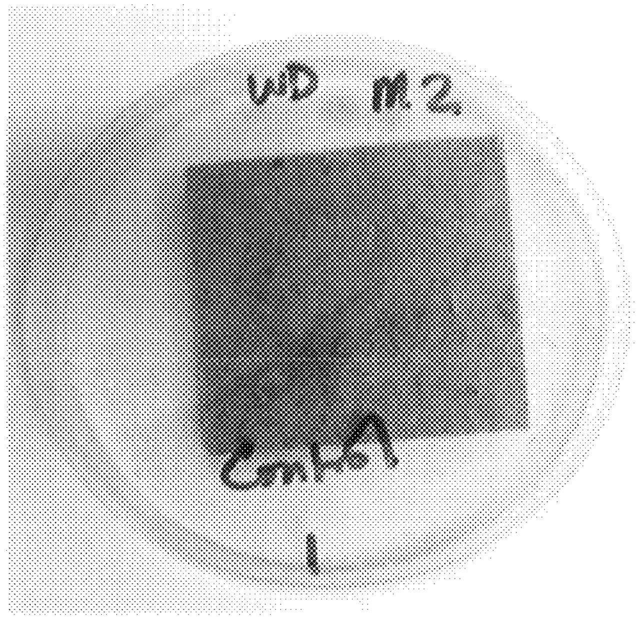
Figure 11F:
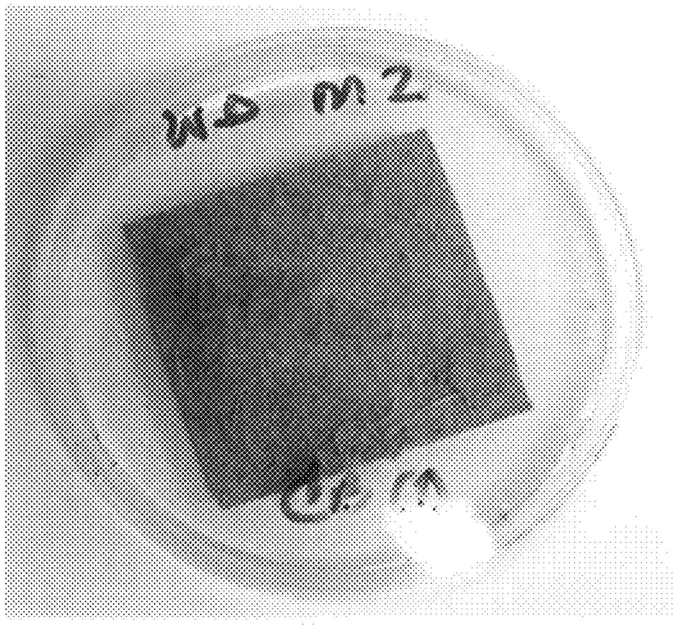

Three concentrations of the composition (FB) were used (30%, 60% and 100%). Dilutions were made with distilled water. Aqueous solutions of chlorine bleach 3.75%, 7.5% and 12.5% sodium hypochlorite were also used. Treatments were sampled at 0, 1, 5, 30 and 60 minutes. Complete inhibition of spore growth was observed for 30% FB after five (5) minutes. No growth was observed with 60 and 100% FB after one (1) minute as illustrated in FIG. 2. FIGS. 1A-E show the effect of different concentrations of composition FB on the killing of black mold (*Stachybotrys chartarum*) spores. FIG. 1A shows the effect of 100% FB on the reduction of black mold spores. FIG. 1B shows the effect of 60% FB on the reduction of black mold spores. FIG. 10 shows the effect of 50% FB on the reduction of black mold spores. FIG. 1D shows the effect of 40% FB on the reduction of black mold spores. FIG. 1E shows the effect of 30% FB on the reduction of black mold spores.

Figure 3A:
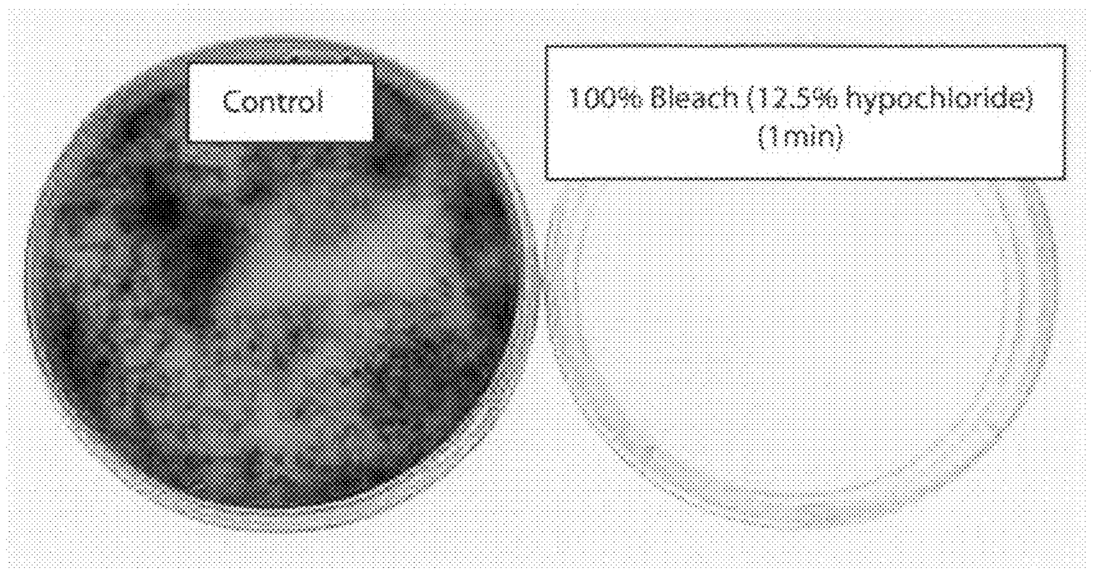
FIGS. 3A-C show the effect of different concentrations of household Clorox® bleach on the killing of black mold (*Stachybotrys chartarum*) spores.
Figure 3B:
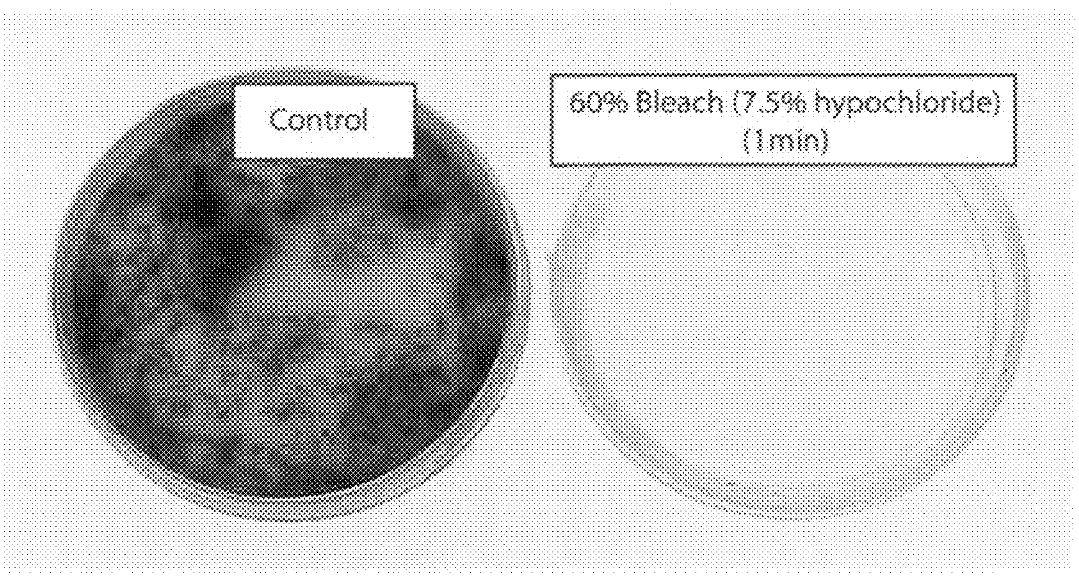
Figure 3C:
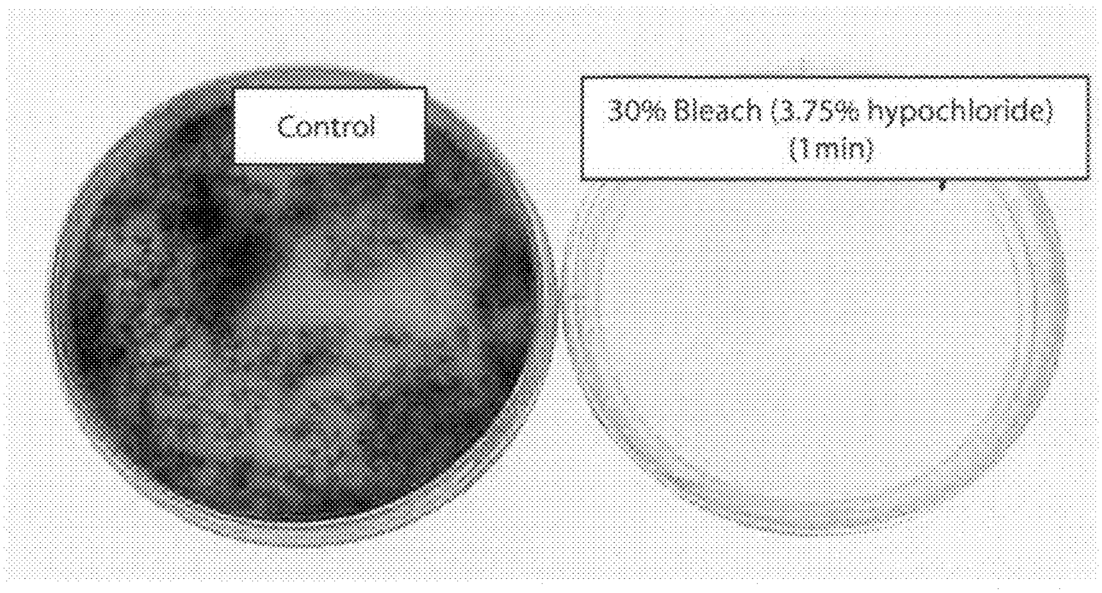
Figure 4:
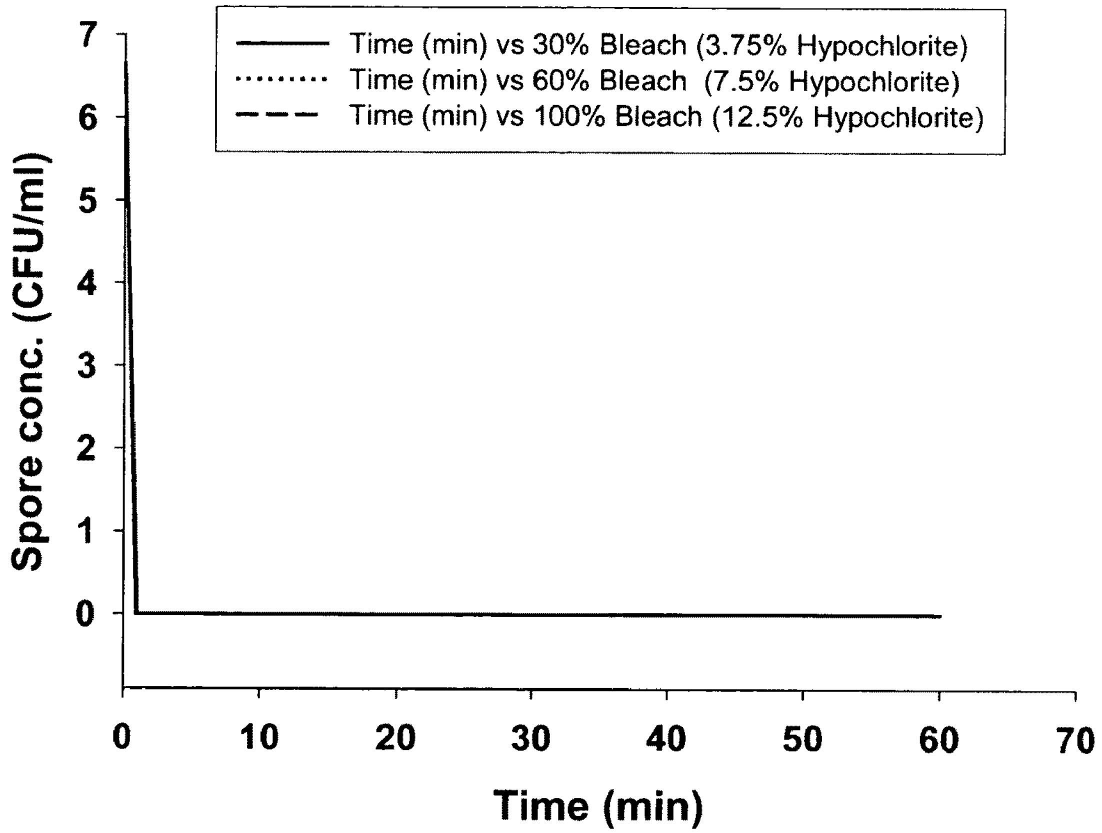
FIG. 4 shows the effect of different concentrations of chlorine bleach (3.75, 7.5, and 12.5% sodium hypochlorite) on the killing of black mold (*Stachybotrys chartarum*) spores.

In the case of chlorine bleach, complete inhibition of spore growth was observed for all three concentrations of detergent used (3.75%, 7.5% and 12.5% sodium hypochlorite) after one (1) minute as illustrated in FIG. 4. FIGS. 3A-C show the effect of different concentrations of household Clorox® bleach on the killing of black mold (*Stachybotrys chartarum*) spores. FIG. 3A shows the effect of 12.5% NaOCl on the killing of black mold spores. FIG. 3B shows the effect of 7.5% NaOCl on the killing of black mold spores. FIG. 3C shows the effect of 3.75% NaOCl on the killing of black mold spores.

The results from these tests clearly indicate that the composition of the present invention is very effective in the decontamination of black mold spores. It is also clear that bleach is very effective decontaminant. The primary motivation for finding a replacement for bleach is due to its high corrosiveness and not its inability to kill germs. Composition (FB) was then further optimized, and 30%, 40%, 50% and 60% solutions were used to test for the optimum concentration that will prevent spore growth in one (1) minute. Samples were taken at one and five minutes. Growth was observed after five (5) minutes with the 30% concentration as previously observed. The 40% concentration inhibited growth after five (5) minutes and both the 50% and 60% concentrations inhibited growth after one (1) min as seen in Table 2. At this point, a 50% dilution was selected as the optimum concentration of composition (FB) that will inhibit spores within a minute, and this concentration was used in further studies on building materials.

TABLE 2

Effect of different concentrations of composition (FB) on the reduction of black mold (*Stachybotrys chartarum*) spore numbers with time (log CFU/10 ml).

| Treatment | Spore counts 0 min | Spore counts 1 min | Spore counts 5 min |
|---|---|---|---|
| Control | 5.8 | 5.8 | 5.8 |
| 30% FB | 5.8 | 4.75 | 3.7 |
| 40% FB | 5.8 | 3.3 | 0 |
| 50% FB | 5.8 | 0 | 0 |
| 60% FB | 5.8 | 0 | 0 |

Figure 5:
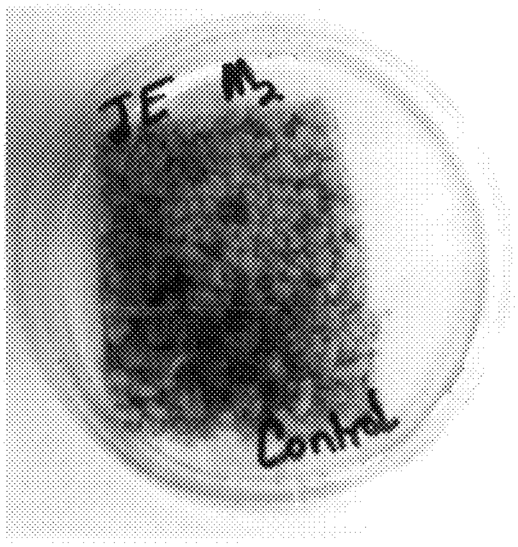
FIG. 5 shows the effect of composition (50% FB) and household Clorox® bleach on carpets inoculated with *Stachybotrys chartarum* spores.
Figure 5:
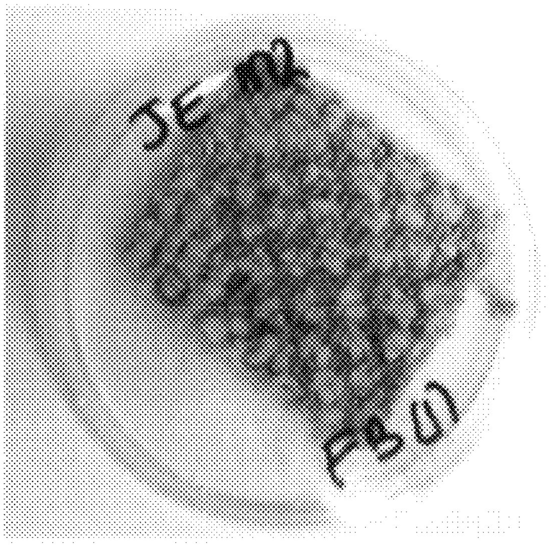
Figure 5:
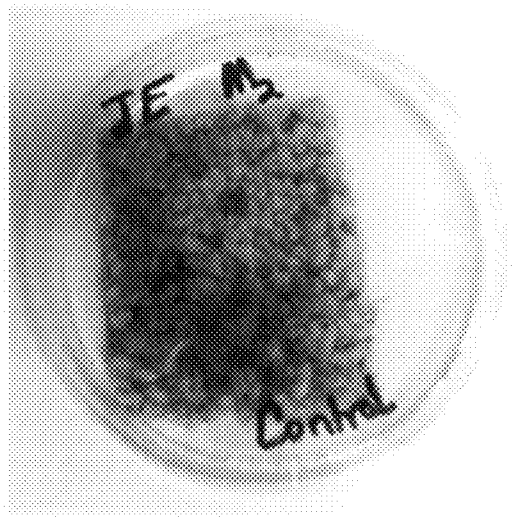
Figure 5:
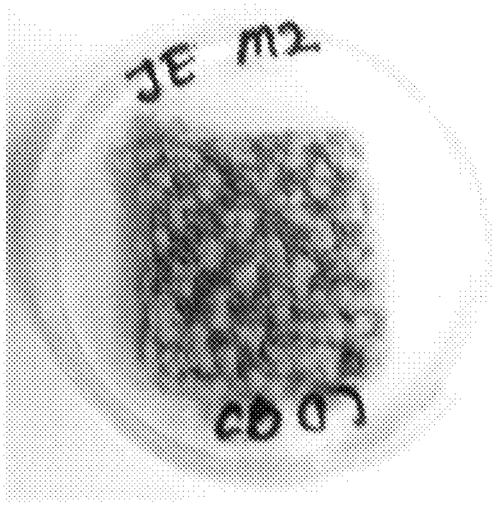
Figure 6:
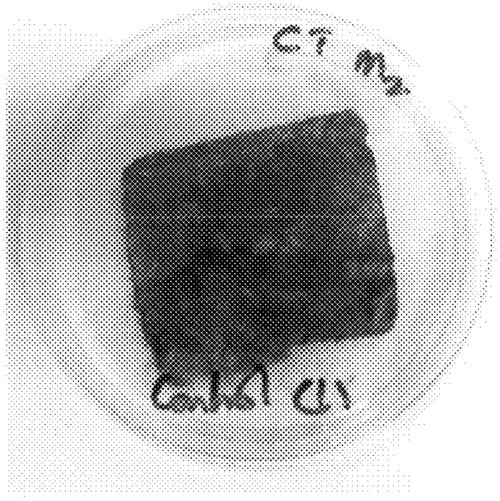
FIG. 6 shows the effect of composition (50% FB) and household Clorox® bleach on ceiling tiles inoculated with *Stachybotrys chartarum* spores.
Figure 6:
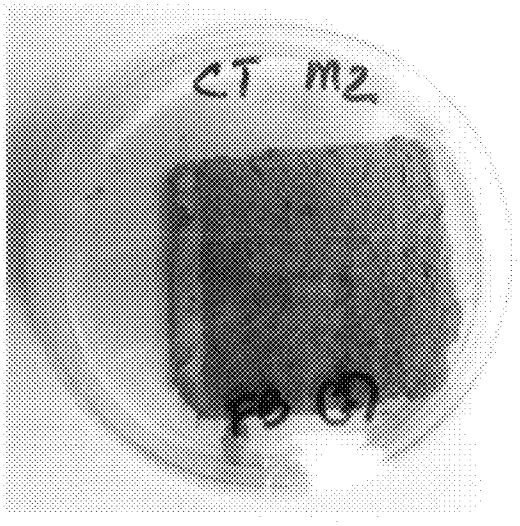
Figure 6:
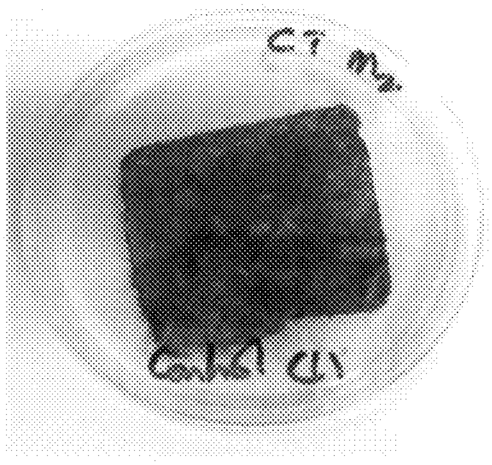
Figure 6:
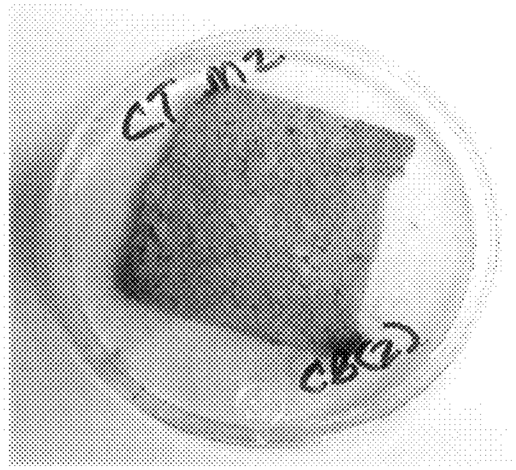
Figure 7:
FIG. 7 shows the effect of composition (50% FB) and household Clorox® bleach on general purpose printing papers inoculated with *Stachybotrys chartarum* spores.
Figure 7:
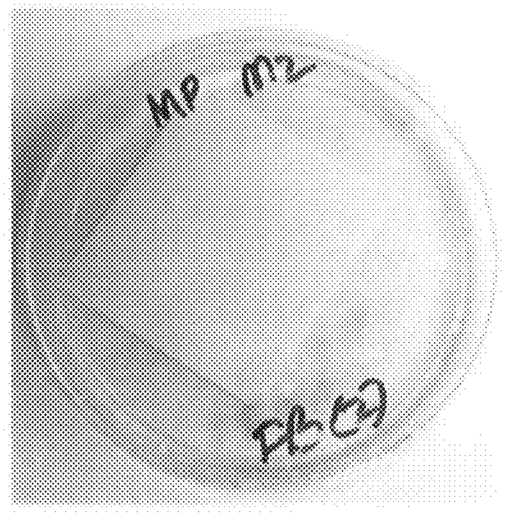
Figure 7:
Figure 7:
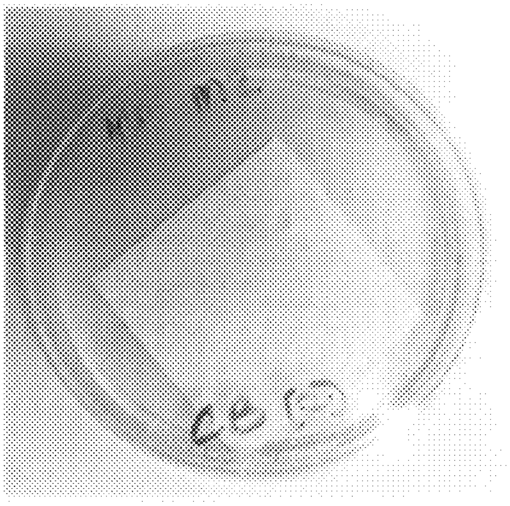

Determination of Treatment Efficacy: Building Materials. The composition has also been demonstrated to be effective in decontaminating a variety of substrate surfaces. Three different materials were obtained from Home Depot® Home Improvement Center (Homer TLC, Inc. Claymont, Del.): 1) carpet (Journey's End Loop Harbor Lig); 2) ceiling tile; 3) general purpose printing paper (white); and 4) wood. The samples were cut into two-inch squares, soaked overnight in ten milliliters (10 ml) deionized water, and sterilized by autoclaving for one hour at 121° C. The sterilized materials were allowed to cool off and were divided into two sets. The first set of sterilized materials was inoculated with 100 μL of spore suspension ($10^7$ spores/10 ml solution) and allowed to air dry under the hood for thirty minutes, then sprayed with about 1 ml of water (control), composition (50% FB) and household Clorox® bleach (Clorox Company, Oakland, Calif.), respectively, and incubated at room temperature in the dark for thirty (30) days. After 30 days, growth was observed in all control treatments (materials treated with water). Growth was not observed on the materials treated with either composition (50% FB) or household Clorox® bleach (FIG. 5, FIG. 6, FIG.

Figure 8:
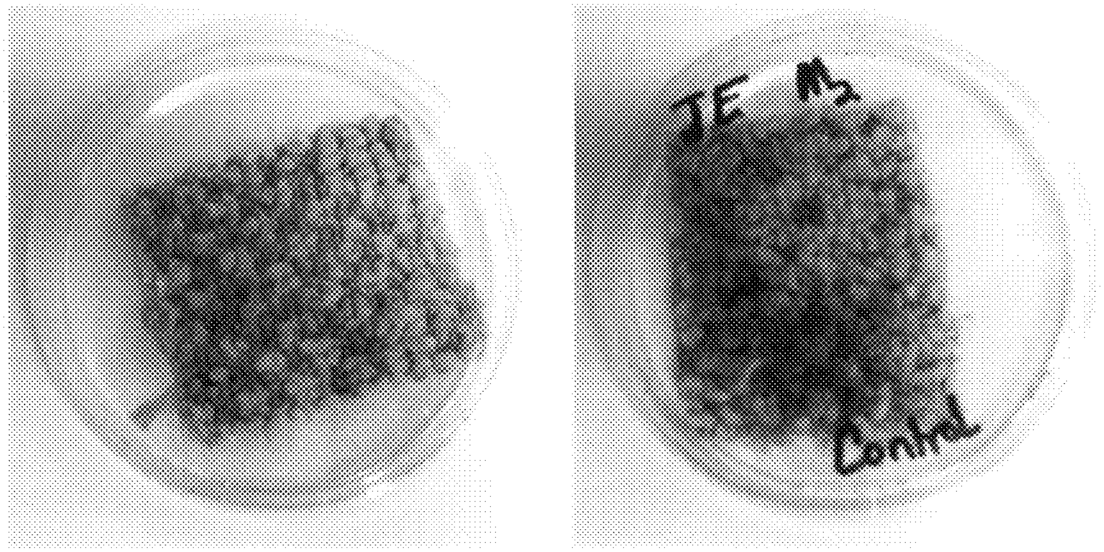
FIG. 8 shows the growth of black mold on carpets inoculated with *Stachybotrys chartarum* spores and incubated for 30 days in the dark.
Figure 9:
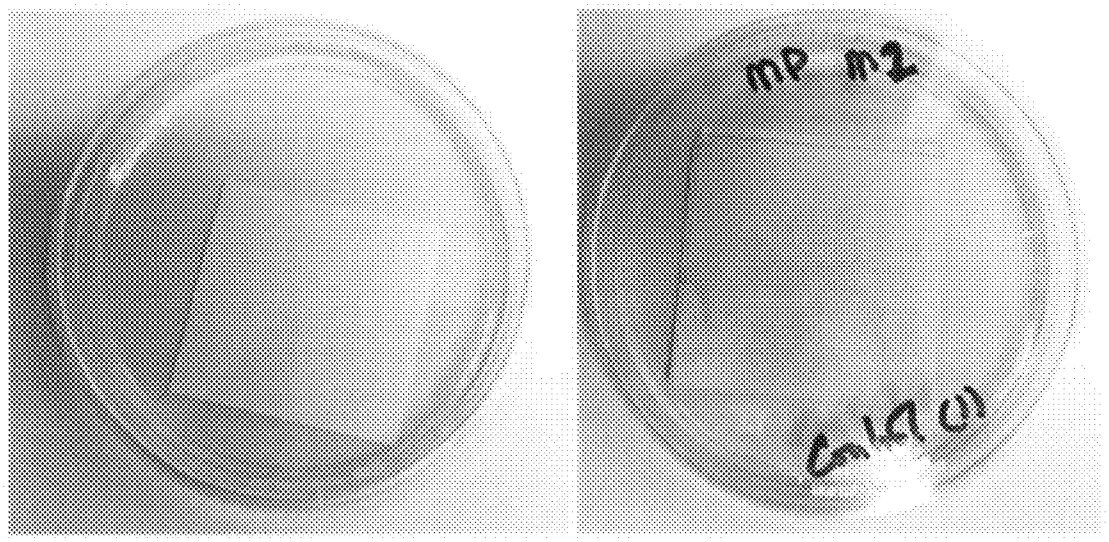
FIG. 9 shows the growth of black mold on general purpose printing papers inoculated with *Stachybotrys chartarum* spores and incubated for 30 days in the dark.

7 and FIGS. 11A-F). The second set of sterilized materials was inoculated with 100 μL of the same concentration of spore suspension ($10^7$ spores/10 ml solution) and incubated at room temperature in the dark for thirty days. Growth was observed in all samples, with growth on the samples were in the following order: ceiling tile>carpet>paper (FIG. 8, FIG. 9 and FIG. 10). These samples were then immersed in thirty milliliters (30 ml) of water (control), the composition (50% FB) and household Clorox® bleach, respectively, for five minutes (5 min) and they were allowed to air dry under the hood for 1.5 hours. The satratoxin was extracted with ten milliliters (10 ml) of methanol. Extracts, about four milliliters (4 ml), were allowed to air dry overnight under the hood to a final volume of about 1.5 ml. A minimum amount (100 μL) from each sample was re-suspended in 900 μL of deionized water, and 8 μl of each treatment/suspension was used for the Yeast Toxicity Assay.

Yeast Toxicity Assay: Cultures of *Kluyveromyces marxianus* (No. 8554; ATCC, Manassas, Va.) were grown at 37° C. and stored at 4° C. on yeast-peptone-glucose (YPG) agar (1% (wt/vol) yeast extract; 1% (wt/vol) bacteriological peptone; 2% (wt/vol) glucose; and 2% (wt/vol) agar). For the assay, a single colony from an agar plate was added to 5 ml of YPG-50 liquid medium (1% (wt/vol) yeast extract; 1% (wt/vol) bacteriological peptone; and 50 mM glucose) in a culture tube. The tube was incubated in a rotary incubator for about sixteen (16) hours at 37° C. to obtain a culture with final density of $1\times10^8$ cells/ml in YPG-50. YPG-50 was supplemented with a stock solution of polymixin B sulfate (PMBS) (ICN Biomedicals, Aurora, Ohio), to give a final concentration of fifteen milligrams per milliliter (15 mg/ml) for the bioassay procedure. The tests were run in triplicate. For the bioassay procedure, 136 microliters (μl) of PMBS-supplemented YPG-50 medium were added to the wells of a 96-well polystyrene microtiter plate. Eight microliters (8 μl) of the test or control sample were added to each well, followed by sixteen microliters (16 μl) of yeast inoculum, to yield an initial cell density of approximately $1\times10^8$ cells/ml. Blank wells (negative control) contained 152 μl of medium and 8 μl of water. Control wells (positive control) contained 144 μl of medium and 16 μl of yeast inoculum. The plates were sealed and incubated on a plate shaker at 37° C. for eight hours (when cells reach stationary phase). Cell density was measured every two hours by measuring the absorbance in a microtiter plate reader at a wavelength of 570 nm. The absorbance was correlated with *K. marxianus* 8-hour growth curve to determine cell density. These cultures are sensitive to trichothecene mycotoxins, and will not grow in the presence of very small quantities (100-200 ng/ml). A high optical density (OD) will be as a result of increased turbidity, which will signify growth of the organism, and a low OD will be due to little or no growth of the organism. The OD value of all the treatments (medium+(composition (50% FB) or household Clorox® bleach treatment)+yeast inoculum) was higher than of their positive controls (medium+water treatment+yeast inoculum) at all the sampled time points (0, 2, 4, 6.5 and 8 hours). This showed that composition (50% FB) was able to degrade the toxins in the building materials within five minutes (5 min), and thus methanol extraction of the detoxified materials did not yield any traces of satratoxin, compared to the water treated samples (Tables 3, 4, 5).

TABLE 3

Optical density (570 nm) of carpet samples treated with composition (50% FB) and household Clorox ® bleach (CB) after mold growth.

| Time (h) | Positive Control | Control | 50% FB | CB |
|---|---|---|---|---|
| 0 | 0.335 | 0.395 | 0.952 | 0.35 |
| 2 | 0.33 | 0.292 | 0.912 | 0.325 |
| 4 | 0.319 | 0.293 | 0.808 | 0.37 |
| 6.5 | 0.318 | 0.301 | 0.714 | 0.436 |
| 8 | 0.318 | 0.301 | 0.714 | 0.436 |

TABLE 4

Optical density (570 nm) of multi-purpose paper samples treated with composition (50% FB) and household Clorox ® bleach (CB) after mold growth.

| Time (h) | Positive Control | Control | 50% FB | CB |
|---|---|---|---|---|
| 0 | 0.335 | 0.399 | 0.645 | 0.490 |
| 2 | 0.33 | 0.381 | 0.60 | 0.474 |
| 4 | 0.319 | 0.44 | 0.614 | 0.470 |
| 6.5 | 0.318 | 0.497 | 1.008 | 0.482 |
| 8 | 0.318 | 0.497 | 1.008 | 0.482 |

TABLE 5

Optical density (570 nm) of ceiling tile samples treated with composition (50% FB) and household Clorox ® bleach (CB) after mold growth.

| Time (h) | Positive Control | Control | 50% FB | CB |
|---|---|---|---|---|
| 0 | 0.335 | 0.318 | 0.811 | 0.472 |
| 2 | 0.33 | 0.296 | 0.895 | 0.456 |
| 4 | 0.319 | 0.350 | 0.798 | 0.530 |
| 6.5 | 0.318 | 0.424 | 0.699 | 0.596 |
| 8 | 0.318 | 0.424 | 0.699 | 0.596 |

Example 2

The antimicrobial effect on *Stachybotrys chartarum* spores using compositions with pre-made fatty acid soaps and fatty acid soaps generated in situ by neutralizing the free fatty acids with an excessive amount of alkalinating agent was investigated.

TABLE 6

| Component (I) | Composition (I) | Amount (I) |
|---|---|---|
| Alkanol (ml): | Ethanol | 62 |
| Free fatty acid (mole): | Lauric acid | 0.05 |
| Alkalinating agent (mole): | Potassium hydroxide | 0.06 |
| Water (ml): | Deionized | 26 |
| pH: | | 14.42 |

The mixture was made up to a volume of 100 ml with deionized water.

The killing of *Stachybotrys chartarum* spores by the composition of Table 6 was complete.

TABLE 7

| Component (II) | Composition (II) | Amount (II) |
|---|---|---|
| Alkanol (ml): | Ethanol | 62 |
| Fatty acid soaps (mole): | Potassium laurate | 0.05 |
| Alkalinating agent (mole): | Potassium hydroxide | 0.01 |

TABLE 7-continued

| Component (II) | Composition (II) | Amount (II) |
|---|---|---|
| Water (ml): | Deionized | 26 |
| pH: | | 14.42 |

The mixture was made up to a volume of 100 ml with deionized water.

The killing of *Stachybotrys chartarum* spores by the composition of Table 7 was complete.

Thus, there was no difference in the antimicrobial effect between compositions using pre-made fatty acids soaps and fatty acid soaps generated in situ by adding an excessive amount of alkalinating agent to neutralize the free fatty acids. In subsequent experiments, fatty acid soaps were generated in situ.

Example 3

Bacterial spores are highly resistant to chemical and physical agents. They are recognized as the most difficult microorganisms to kill. The most important spore forming bacteria are members of the genera *Bacillus* and *Clostridium*. *Bacillus anthracis* and *Clostridium difficile* have nearly a worldwide distribution. Large outbreaks of *Clostridium difficile* have been described in hospitals. The spores of this pathogen are able to survive for long periods in hospital environments, e.g., on floors and around toilets. *Bacillus* spores, which are abundant in the soil, cause infection in farm and wild animals, and human who are in contact with infected animals or ingested contaminated meat. *Bacillus anthracis* spores have been recognized as a very dangerous biological warfare agent. It is extremely important to find an efficient control measure to neutralize these infectious agents. The sterilizing effect of the compositions of this invention was examined on *Bacillus atropheus* spores adhering to the surface of stainless steel discs. *Bacillus atropheus*, a well known surrogate for *Bacillus anthracis*, was used in all the experiments. Triplicate samples (three separate disks) are performed for all treatments and time points.

Procedure for Quantitative Viable Spore Population Assay on Stainless Steel Discs.

Materials: Stainless steel discs inoculated with $2\times10^6$ spores of *Bacillus atropheus* per disk (SGM Biotech Inc); Sterile 6 mm glass beads; 0.1% Tween 80 in water; and Tryptic soy agar plates.

Experimental procedure: Place a single inoculated disc in a sterile flat-bottomed scintillation vial. Add 10 ml of treatment (water, composition of the present invention, etc.) and incubate at room temperature for specified time (15 sec, 5 min, 30 min, etc.). After treatment, remove disc with flamed forceps and blot by touching one edge of the disk on sterile filter paper to remove excess treatment. Place treated disc in a flat-bottom test tube (21.5×95 mm) filled with four 6 mm glass beads and 5.0 ml of 0.1% Tween 80. Sonicate each tube for 5 minutes and then vortex each tube for 5 minutes (at speed 5 on a Vortex Genie 2). Add 5.0 ml sterile purified water and vortex again for five minutes. Heat shock at 82° C. for ten minutes. Vortex the heat-shocked tubes for ten seconds. Perform serial tenfold dilutions by transferring 0.1 ml to dilution tubes containing 0.9 ml sterile water. Vortex each tube for ten seconds. Plate 1.0 ml of the initial heat-shocked tube, as well as 0.1 ml of the initial heat-shocked tube and of each dilution, in triplicate on tryptic soy agar plates. Incubate plates at 32° C. Count colonies recovered after 24, 48, and 72 hours of incubation. Finally, calculate percent survival and percent killing in comparison to control disks incubated in water only.

Procedure for Qualitative Spore Survival Assay.

Materials: Stainless steel discs inoculated with $2\times10^6$ spores of *Bacillus atropheus* per disk (SGM Biotech Inc.); and Tryptic soy broth.

Experimental procedure: Place a single inoculated disc in a sterile flat-bottomed scintillation vial. Add 10 ml of treatment (water, composition of the present invention, etc) and incubate at room temperature for specified time (15 sec, 5 min, 30 min, etc.). After treatment, remove disc with flamed forceps and blot by touching one edge of the disk on sterile filter paper to remove excess treatment. Place treated disc in 50 ml sterile screw capped test tube containing ten milliliters (10 ml) of tryptic soy broth. Incubate the tubes at 32° C. Each day for fourteen days or until all tubes have reached maximum turbidity, then observe tubes for growth by comparing turbidity to MacFarland turbidity standards. Score from 0-7 with 0=no visible growth and 7=dense growth. Once a tube reaches a score of 7, it is recorded as a 7 for the remainder of the experiment.

Qualitative analysis of spore killing by the inventive composition: Eleven compositions were tested qualitatively for their ability to kill spores of *Bacillus* atropheus, as shown in Table 8. Three stainless steel disks inoculated with $2\times10^6$ *B. atropheus* spores were individually exposed to each formulation for thirty (30) minutes at room temperature. Exposed disks were removed from treatment, blotted to remove excess treatment, placed in 10 ml of tryptic soy broth growth medium, and incubated at 32° C. Cultures were observed for growth daily for fourteen days. Results of these experiments, shown in Table 9, were recorded as the sum of the scores for three separate cultures for each treatment; maximum score=21. A score of 6 or higher indicates significant growth.

TABLE 8

| Combination of compositions of different constituents | | | | | |
|---|---|---|---|---|---|
| Compositions | Lauric acid (g) | KOH (g) | EDTA (g) | Ethanol (ml) | pH |
| 1 | 10 | 3.5 | 0 | 62 | 14.42 |
| 2 | 10 | 4.24 | 1 | 62 | 14.4 |
| 3 | 10 | 4.25 | 2 | 62 | 10.2 |
| 4 | 10 | 5.01 | 2 | 62 | 14.21 |
| 5 | 10 | 6.5 | 4 | 62 | 11.04 |
| 6 | 10 | 5.5 | 0 | 62 | 14.94 |
| 7 | 10 | 8.6 | 0 | 62 | 15.27 |
| 8 | 17.5 | 7.6 | 0 | 56.3 | 14.87 |
| 9 | 0 | 0 | 0 | 62 | 7 |
| 10 | 0 | 0.56 | 0 | 62 | 14.02 |
| 11 | 10 | 0 | 0 | 62 | 4.61 |

The mixture was made up to a volume of 100 ml with deionized water.

TABLE 9

| Results of the sporicidal activity of different compositions | | | |
|---|---|---|---|
| Compositions | Maximum score | Days required to reach max. score | Days required to reach significant. score |
| 1 | 21 | 4 | 2 |
| 2 | 21 | 3 | 2 |
| 3 | 21 | 2 | 1 |
| 4 | 21 | 4 | 3 |
| 5 | 21 | 13 | 1 |
| 6 | 3 | 3 | NA |
| 7 | 3 | 4 | NA |
| 8 | 3 | 3 | NA |
| 9 | 21 | 2 | 1 |

TABLE 9-continued

| Results of the sporicidal activity of different compositions | | | |
|---|---|---|---|
| Compositions | Maximum score | Days required to reach max. score | Days required to reach significant. score |
| 10 | 21 | 3 | 3 |
| 11 | 21 | 3 | 2 |
| Water | 21 | 1 | 1 |

These results suggest that compositions 6, 7, and 8 are the most effective. The chelating agent EDTA has a very detrimental effect on the sporicidal effect of the compositions. The results for these tests clearly show a synergism between potassium laurate, ethanol, and KOH, which account for the dramatic sporicidal effect of the compositions. It is seen from these results that the use of the three ingredients in combination (i.e. ethanol, fatty acid soaps, and alkalinating agent) produced a much stronger synergistic sterilizing effect than could be expected from the individual or conjoint use of ethanol and alkalinating agents or the conjoint use of ethanol and free lauric acid, and could markedly reduce the required concentrations of the individual ingredients. The antimicrobial compounds of the composition work synergistically to decrease both the concentration of individual compounds required for inactivating pathogens and, as importantly, greatly reduce the time needed for pathogen inactivation. The more rapidly pathogens are inactivated the less likely they are to establish an infection. Surprisingly, we found that the total antimicrobial effect provided by the composition appears to be far more than can be elucidated by examining the antimicrobial effect of each compound individually.

Quantitative analysis of spore killing by the inventive compositions 1, 6, 8, and 11: Four compositions were tested for their ability to kill spores of *Bacillus* atropheus, using a quantitative assay to measure the number of spores surviving treatment. Three stainless steel disks inoculated with $2\times10^6$ *B. atropheus* spores were individually exposed to each composition for either seconds or 30 minutes at room temperature. Exposed disks were removed from treatment and processed to remove spores from the disks. Spore suspensions removed from the disks were diluted and dilutions plated in triplicate on tryptic soy agar plates. Plates were incubated for 72 hours at 32° and colonies counted at 24, 48, and 72 hours. Results for these experiments, presented as the average of three replicate samples are shown in Table 10.

TABLE 10

| Percent reduction of *Bacillus atropheus* spores using selected compositions | | |
|---|---|---|
| Composition | Viable spores | % Killing after |
| 1 | $6.9 \times 10^2$ | 99.96% |
| 6 | No growth | >99.99995% |
| 8 | No growth | >99.99995% |
| 11 | $5.2 \times 10^5$ | 74% |
| Water control | $2 \times 10^6$ | 0% |

These results demonstrate that formulas 6 and 8 yield complete or almost complete killing of $2\times10^6$ spores in 30 minutes at room temperature.

Example 4

Insect vector (e.g., mosquitoes, etc.) control is an integral part of controlling the transmission of infectious diseases (West Nile, malaria, encephalitis, etc.). The compositions of the present invention are effective in killing the pathogens that cause these infectious diseases as well as the vectors that transmit these pathogens and, therefore lead to a reduced infectious disease risk. Insecticide toxicity has increased interest in alternative and integrated implementation of vector control methods that include biological control. The composition of the present invention is not toxic and safe for humans and the environment and need no rinsing for surfaces with direct contact with food, because it is made with GRAS ingredients.

TABLE 11

| Component | Composition | Amount |
|---|---|---|
| Alkanol (ml): | Ethanol | 62 |
| Fatty acid (g): | Lauric acid | 10 |
| Alkalinating agent (g): | Potassium hydroxide | 5.5 |
| | Potassium bicarbonate | 1 |
| pH: | | 14.94 |

The mixture is made up to a volume of 100 ml with deionized water.

Insecticidal activity is determined using third instar larvae of the mosquito *Culex pipiens quinquefasciatus*. Ten larvae are placed in a six ounce paper cup containing 100 ml of the composition of the present invention. The treated larvae are stored at 70° F. and 48 hours later the mortalities are recorded.

Example 5

Chemical warfare agents which are likely to pose threat from terrorists include sarin (O-isopropyl methylphosphonofluoridate), soman (O-pinacolyl methylphosphonofluoridate), tabun (O-ethyl N,N-dimethyl phosphoramidocyanidate) and VX (O-ethyl S-2-diisopropylaminoethyl methyl phosphonothiolate). The chemical structures of these agents illustrate the similarity in the fact that they are phosphorus containing compounds and can be chemically altered by nucleophilic attack, using the composition of the present invention, and thereby neutralized as chemical warfare agents.

TABLE 12

| Component | Composition | Amount |
|---|---|---|
| Alkanol (ml): | Ethanol | 72 |
| Fatty acid (g): | Lauric acid | 10 |
| Alkalinating agent (g): | Potassium hydroxide | 5.5 |
| | Aluminum hydroxide | 1 |
| pH: | | 14.94 |

The mixture is made up to a volume of 100 ml with deionized water.

The alkalinating agents are added to the composition in an amount up to 1-3 times more than is sufficient to neutralize the free fatty acids present. The excessive amount is added beyond the neutralization of lauric acid to provide enough nucleophiles to hydrolyze chemical warfare agents and denature infectious prions. The nucleophiles in this inventive composition comprise hydroxides and alkoxides. The alkalinating agents react with ethanol to produce ethoxide. Ethoxide is more alkaline than hydroxides and stronger.

The following test procedure is used to measure the reaction rate: All tests are conducted with CASARM-grade agents (Chemical Agent Standard Analytical Reference Material). All tests are conducted at room temperature in a jacketed reaction vessel equipped with a mixer. The composition of the present invention (100 ml) is placed in the reaction vessel and stirred. At the beginning of the test, two milliliters (2 ml) of the chemical warfare agent is placed in the reaction vessel. Samples are removed from the mixing vessel at different time points. The samples are quenched with solvent and are analyzed by gas chromatography mass spectrometry (GC MS) for unreacted agent. All test samples are analyzed in triplicate.

Example 6

Glass slides artificially contaminated with tissue sections are obtained at autopsy from a human subject with sporadic Creutzfeldt-Jacob disease (with the absence of germline prion protein gene (PRNP) mutation, homozygous methionine at PRNP codon 129), are exposed to 1 min and 10 minute treatments with the following compositions shown in Table 13 at room temperature.

TABLE 13

Combination of compositions of different constituents.

| Compositions | Lauric acid (g) | KOH (g) | Ethanol (ml) | pH |
|---|---|---|---|---|
| 1 | 10 | 3.5 | 62 | 14.42 |
| 6 | 10 | 5.5 | 62 | 14.94 |
| 8 | 17.5 | 7.6 | 56.3 | 14.87 |

The mixture is made up to a volume of 100 ml with deionized water.

Following exposure, tissue is homogenized in lysis buffer as described by Castelleni et al., (1996). Control CJD tissue and tissue exposed the compositions reported in Table 13 subsequently are treated with 2× sample buffer and boiled for ten minutes. A control CJD sample is also subjected to limited proteolysis (100 micrograms/ml proteinase K) for one hour at 37° C., protease inhibitor (Pefabloc, Roche Applied Science, Indianapolis, Ind.) stops the reaction and equal volume of 2× sample buffer is added followed by boiling for ten minutes. All samples are then loaded on 12% polyacrylamide minigel and are electrophoresed at 150V, before transferring to an Immobilon® transfer membrane (Millipore Corporation, Billerica, Mass.) for two hours at 4° C. The samples on the membrane are reacted with monoclonal antibody 3F4, which recognizes the residues 109-112 of human prion protein. Immunoreactivity is visualized by chemiluminescence and detected by standard autoradiography.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

I claim:

1. A method for sanitizing a material which comprises:

(a) providing an aqueous composition which comprises a mixture of a lower alkanol containing 1 to 6 carbon atoms and a fatty acid derivative which is a salt or ester at a pH of about 14 or above, wherein the fatty acid derivative is between about 0.1% and 25% by weight of the composition;

(b) applying the composition to the material in an effective amount to sanitize the material; and (c) optionally removing a resulting composition of step (b).

2. The method of claim 1 wherein the fatty acid derivative is an alkali or alkaline earth metal salt.

3. The method of claim 2 wherein the fatty acid is a sodium (Na), potassium (K), lithium (Li), calcium (Ca) or magnesium (Mg) salt.

4. The method of claim 2 wherein the fatty acid derivative is an alkali or alkaline metal salt of a fatty acid comprising 4 to 22 carbon atoms.

5. The method of claim 4 wherein the fatty acid derivative is an alkali or alkaline metal salt of lauric acid.

6. The method of claim 1 wherein the fatty acid derivative is potassium laurate.

7. The method of claim 1 wherein the fatty acid derivative is an ester selected from the group consisting of a butyl ester, ethyl ester, methyl ester, fatty acyl-Coenzyme A, sucrose ester and a monoglyceride.

8. The method of claim 7 wherein the monoglyceride comprises a glycerol moiety attached by ester or ether linkage to one or more fatty acids having from 4 to 22 carbon atoms or to one or more saturated or unsaturated fatty alcohols having from 8 to 16 carbon atoms.

9. The method of claim 1 wherein the toxin on the material sanitized is a *Stachybotrys* toxin.

10. The method of claim 1 wherein the microorganism or other infectious agent on the material sanitized is a fungus, a bacterium, a fungal spore, a bacterial spore, a virus or a conformationally altered prion.

11. The method of claim 10 wherein the fungal spore on the material sanitized is a *Stachybotrys chartarum* spore.

12. The method of claim 10 wherein the bacterial spore on the material sanitized is a *Bacillus atropheus* spore.

13. The method of claim 1 wherein the chemical warfare agent on the material sanitized is VX, mustard, sarin, soman, or tabun.

14. The method of claim 10 wherein the conformationally altered prion on the material sanitized is selected from the group consisting of CJD, CWD, BSE, and Scrapie.

15. A composition which comprises in a mixture:

(a) a lower alkanol containing 1 to 6 carbon atoms; and (b) a fatty acid derivative which is a salt or ester soluble in the alkanol, wherein the composition has a pH of 14 or above and wherein the fatty acid derivative is between about 0.1% to 25% by weight of the composition.

16. The composition of claim 15 is an aqueous solution.

17. The composition of claim 15 wherein the lower alkanol is methanol, ethanol, n-propanol, isopropanol, n-butanol or mixtures thereof.

18. The composition of claim 15 wherein the fatty acid derivative is an alkali or alkaline earth metal salt.

19. The composition of claim 18 wherein the fatty acid is a sodium (Na), potassium (K), lithium (Li), calcium (Ca) or magnesium (Mg) salt.

20. The composition of claim 18 wherein the fatty acid derivative is an alkali or alkaline metal salt of a fatty acid comprising 4 to 22 carbon atoms.

21. The composition of claim 20 wherein the fatty acid derivative is an alkali or alkaline metal salt of lauric acid.

22. The composition of claim 21 wherein the fatty acid derivative is potassium laurate.

23. The composition of claim 15 wherein the fatty acid derivative is an ester selected from the group consisting of a butyl ester, ethyl ester, methyl ester, fatty acyl-Coenzyme A, sucrose ester and a monoglyceride.

24. The composition of claim 23 wherein the monoglyceride comprises a glycerol moiety attached by ester or ether linkage to one or more fatty acids having from 4 to 22 carbon atoms or to one or more saturated or unsaturated fatty alcohols having from 8 to 16 carbon atoms.

25. The composition of claim 15 further comprising one or more ingredients selected from the group consisting of thickeners, emollients, moisturizers, corrosion inhibitors, propellants, perfumes, flavoring agents, defoamers, antioxidants and dyes.

26. A method of treating a material, which comprises:

(a) providing an aqueous composition which comprises a mixture of a lower alkanol containing 1 to 6 carbon atoms and a fatty acid derivative which is a salt or ester at a pH of about 14 or above, wherein the fatty acid derivative is between about 0.1% and 25% by weight of the composition; and (b) applying the composition to the material in an effective amount to treat the material.

27. The method of claim 26 wherein a resulting composition of step (b) is removed from the material.

28. A method of making a composition, which comprises:

(a) providing a lower alkanol containing 1 to 6 carbon atoms;

(b) providing a fatty acid derivative which is a salt or ester soluble in the alkanol; and (c) mixing the lower alkanol and fatty acid derivative to provide the composition, wherein the composition has a pH of 14 or above and wherein the fatty acid derivative is between about 0.1% to 25% by weight of the composition.

29. The method of claim 28 wherein the lower alkanol is ethanol.

30. The method of claim 28 wherein the fatty acid derivative is an alkali or alkaline earth metal salt.

31. The method of claim 30 wherein the fatty acid is a sodium (Na), potassium (K), lithium (Li), calcium (Ca) or magnesium (Mg) salt.

32. The method of claim 30 wherein the fatty acid derivative is an alkali or alkaline metal salt of a fatty acid comprising 4 to 22 carbon atoms.

33. The method of claim 32 wherein the fatty acid derivative is an alkali or alkaline metal salt of lauric acid.

34. The method of claim 28 wherein the fatty acid derivative is potassium laurate.

35. The method of claim 28 wherein the fatty acid derivative is an ester selected from the group consisting of a butyl ester, ethyl ester, methyl ester, fatty acyl-Coenzyme A, sucrose ester and a monoglyceride.

36. The method of claim 35 wherein the monoglyceride comprises a glycerol moiety attached by ester or ether linkage to one or more fatty acids having from 4 to 22 carbon atoms or to one or more saturated or unsaturated fatty alcohols having from 8 to 16 carbon atoms.

37. A method of making a composition, which comprises:

(a) providing a lower alkanol containing 1 to 6 carbon atoms;

(b) providing a fatty acid;

(c) providing an alkalinating agent; and (d) mixing the lower alkanol, fatty acid and alkalinating agent to provide the composition, wherein the composition has a pH of 14 or above and wherein the fatty acid derivative is between about 0.1% to 25% by weight of the composition.

38. The method of claim 32 wherein the lower alkanol is ethanol.

39. The method of claim 32 wherein the fatty acid is a fatty acid comprising 4 to 22 carbon atoms.

40. The method of claim 32 wherein the fatty acid is lauric acid.

41. The method of claim 32 wherein the alkalinating agent is selected from the group consisting of an alkali metal hydroxide, alkaline earth metal hydroxides, alkali metal or hydrogen carbonates and mixtures thereof.

42. The method of claim 32 wherein the alkalinating agent is selected from the group consisting of ammonium hydroxide, aluminum hydroxide, sodium hydroxide, potassium hydroxide, lithium hydroxide, calcium hydroxide, magnesium hydroxide, sodium carbonate, sodium hydrogen carbonate, and mixtures thereof.

* * * * *